(12) United States Patent
Bager et al.

(10) Patent No.: US 12,274,813 B2
(45) Date of Patent: Apr. 15, 2025

(54) URINARY CATHETER

(71) Applicant: Coloplast A/S, Humlebaek (DK)

(72) Inventors: Kim Bager, Lyngby (DK); Frederik Seier Wermuth Thingbak, Gilleleje (DK)

(73) Assignee: Coloplast A/S, Humlebaek (DK)

( * ) Notice: Subject to any disclaimer, the term of this patent is extended or adjusted under 35 U.S.C. 154(b) by 841 days.

(21) Appl. No.: 17/428,987

(22) PCT Filed: Feb. 7, 2020

(86) PCT No.: PCT/DK2020/050032
§ 371 (c)(1),
(2) Date: Aug. 6, 2021

(87) PCT Pub. No.: WO2020/160738
PCT Pub. Date: Aug. 13, 2020

(65) Prior Publication Data
US 2022/0118161 A1    Apr. 21, 2022

(30) Foreign Application Priority Data

| Feb. 8, 2019 | (DK) | ............................ PA 2019 70088 |
| Feb. 8, 2019 | (DK) | ............................ PA 2019 70089 |
| Feb. 8, 2019 | (DK) | ............................ PA 2019 70090 |
| Feb. 8, 2019 | (DK) | ............................ PA 2019 70091 |
| Feb. 8, 2019 | (DK) | ............................ PA 2019 70092 |

(51) Int. Cl.
*A61M 25/00* (2006.01)
*A61L 29/08* (2006.01)
(Continued)

(52) U.S. Cl.
CPC ......... *A61L 29/08* (2013.01); *A61M 25/0045* (2013.01); *A61M 25/007* (2013.01);
(Continued)

(58) Field of Classification Search
CPC ............ A61M 25/007; A61M 25/0015; A61M 2025/0046; A61M 25/0017; A61M 25/0111; A61M 25/0043; A61M 2250/00; A61M 2025/0056; A61M 2025/0059; A61M 2025/006; A61M 2025/0062
See application file for complete search history.

(56) References Cited

U.S. PATENT DOCUMENTS

| 4,212,304 A | 7/1980 | Finney |
| 4,307,723 A | 12/1981 | Finney |

(Continued)

FOREIGN PATENT DOCUMENTS

| CN | 106039533 A | 10/2016 |
| EP | 0740558 A1 | 11/1994 |

(Continued)

*Primary Examiner* — Guy K Townsend
*Assistant Examiner* — Seth Han
(74) *Attorney, Agent, or Firm* — Coloplast Corp., Coloplast A/S; Nick Baumann

(57) ABSTRACT

An intermittent hydrophilic urinary catheter (1) with a hydrophilic coating (9) and comprising a plurality of drainage openings (5) is provided. The outer surface (8) of the tubular portion (1a) forms a projection (410) encircling the openings in the outer surface and extending above the hydrophilic surface (411) when the hydrophilic material is in the non-swelled condition.

24 Claims, 22 Drawing Sheets

(52) U.S. Cl.
CPC ............... *A61M 2025/0046* (2013.01); *A61M 2025/0062* (2013.01)

(56) References Cited

U.S. PATENT DOCUMENTS

| | | | |
|---|---|---|---|
| 4,391,276 A * | 7/1983 | Lazarus | A61M 1/285 604/266 |
| 4,610,657 A | 9/1986 | Densow | |
| 4,643,716 A | 2/1987 | Drach | |
| 4,990,133 A | 2/1991 | Solazzo | |
| 5,021,044 A | 6/1991 | Sharkawy | |
| 5,344,412 A | 9/1994 | Wendell et al. | |
| 5,643,228 A | 7/1997 | Schucart et al. | |
| 5,674,192 A * | 10/1997 | Sahatjian | A61M 16/0481 604/28 |
| 5,980,483 A | 11/1999 | Dimitri | |
| 6,107,004 A | 8/2000 | Donadio, III | |
| 6,280,434 B1 | 8/2001 | Kinoshita et al. | |
| 6,537,480 B1 | 3/2003 | Becker et al. | |
| 6,585,926 B1 | 7/2003 | Mirzaee | |
| 7,670,540 B2 | 3/2010 | Lee | |
| 9,084,870 B2 | 7/2015 | Denigea et al. | |
| 9,352,504 B2 | 5/2016 | Schmid et al. | |
| 9,561,353 B2 | 2/2017 | Lee et al. | |
| 10,195,392 B2 | 2/2019 | Crisostomo et al. | |
| 2003/0191453 A1 | 10/2003 | Velez et al. | |
| 2007/0006964 A1 | 1/2007 | Lee | |
| 2009/0192494 A1 * | 7/2009 | Michishita | A61M 25/0041 604/525 |
| 2009/0287135 A1 | 11/2009 | Michishita et al. | |
| 2010/0249702 A1 * | 9/2010 | Magana | A61M 25/1027 264/41 |
| 2012/0130300 A1 | 5/2012 | Stavchansky et al. | |
| 2012/0179144 A1 | 7/2012 | Carleo | |
| 2013/0116662 A1 | 5/2013 | Schmid et al. | |
| 2013/0158675 A1 | 6/2013 | Hutchins, III et al. | |
| 2014/0180261 A1 | 6/2014 | Nyman et al. | |
| 2016/0051801 A1 | 2/2016 | Vase | |
| 2016/0158490 A1 | 6/2016 | Leeflang et al. | |
| 2016/0166807 A1 | 6/2016 | De Stefano et al. | |
| 2016/0193447 A1 * | 7/2016 | Matthiassen | A61M 39/22 604/544 |
| 2016/0199170 A1 | 7/2016 | Biltz | |
| 2017/0095651 A1 | 4/2017 | Hutchins, III et al. | |
| 2017/0106166 A1 | 4/2017 | Wang et al. | |
| 2017/0281909 A1 | 10/2017 | Northop et al. | |
| 2018/0042549 A1 | 2/2018 | Ho et al. | |
| 2018/0207356 A1 | 7/2018 | Joseph et al. | |
| 2018/0304040 A1 | 10/2018 | Jalgaonkar et al. | |
| 2018/0339129 A1 | 11/2018 | Ganatra et al. | |

FOREIGN PATENT DOCUMENTS

| | | | |
|---|---|---|---|
| EP | 2692388 A1 | 2/2014 | |
| EP | 2745868 A1 * | 6/2014 | ........... A61L 29/085 |
| EP | 3184140 A1 * | 6/2017 | ........ A61M 25/0015 |
| GB | 2156223 A * | 10/1985 | .......... A61M 25/007 |
| WO | 2006074283 A2 | 7/2006 | |
| WO | 09049823 A1 | 4/2009 | |
| WO | 09103815 A1 | 8/2009 | |
| WO | 2011011023 A1 | 1/2011 | |
| WO | WO-2011109393 A1 * | 9/2011 | ............. A61F 2/042 |
| WO | 2015019056 A1 | 2/2015 | |
| WO | 2017108879 A1 | 6/2017 | |
| WO | 2018200050 A1 | 11/2018 | |

* cited by examiner

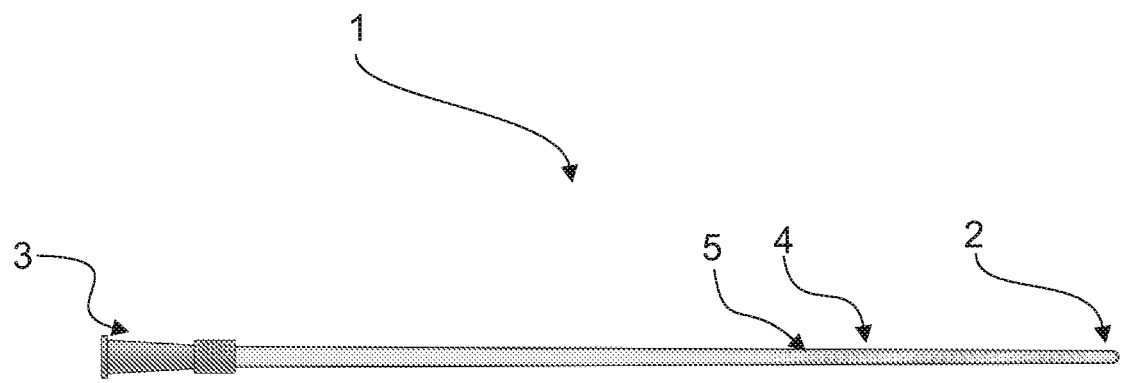
Fig. 5
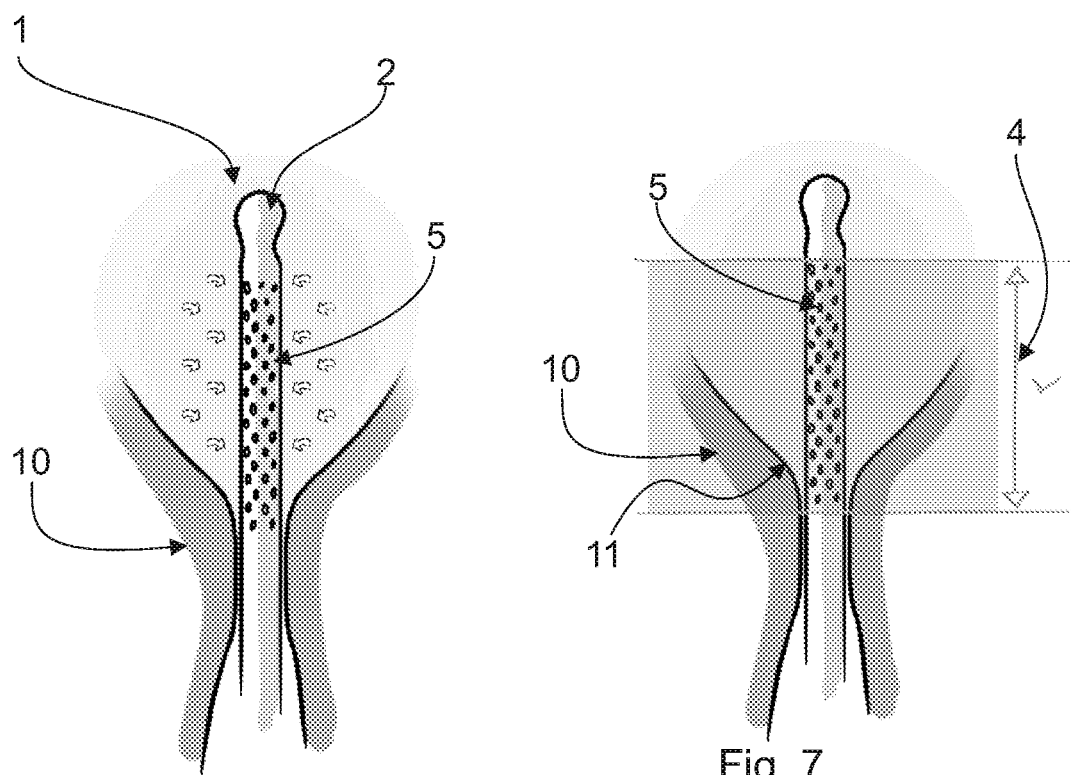
Fig. 6
Fig. 7

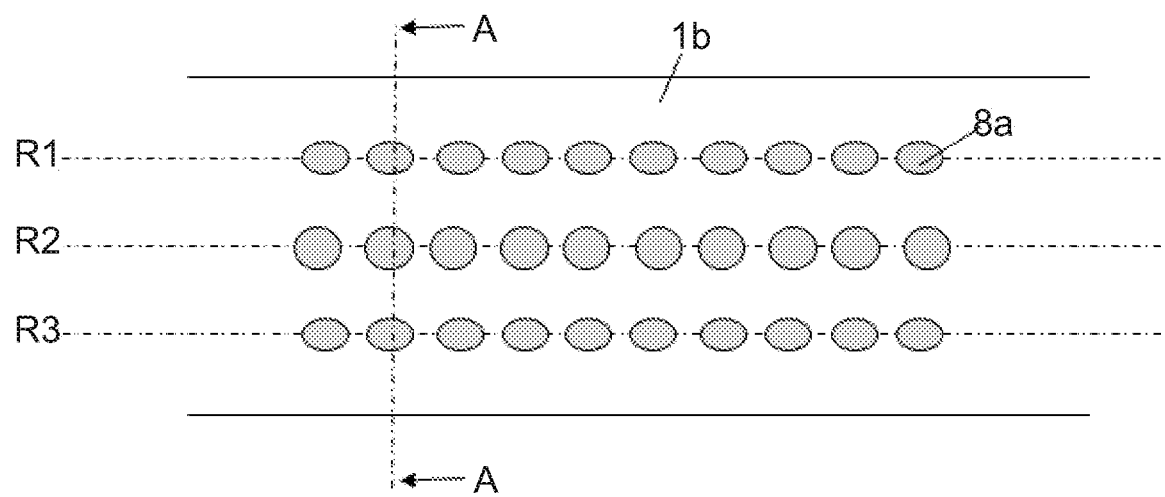
Fig. 15
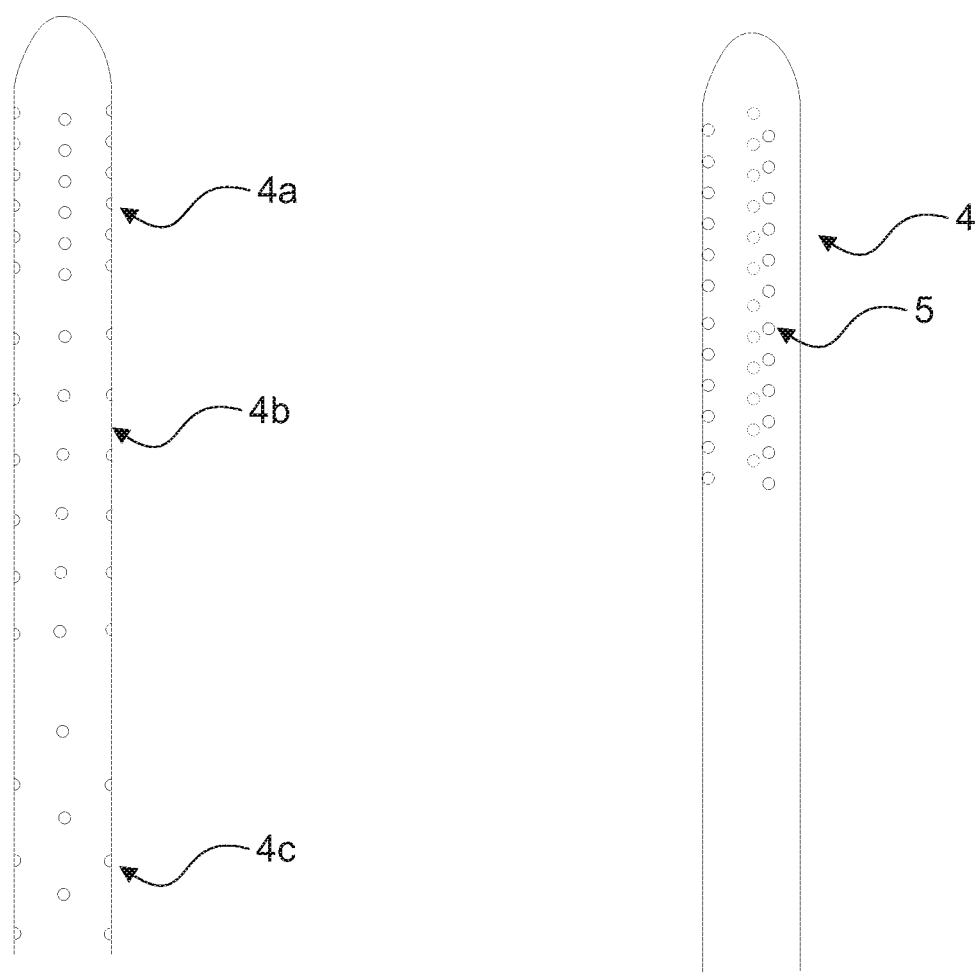
Fig. 16A
Fig. 16B

URINARY CATHETER

The present disclosure relates to an intermittent hydrophilic urinary catheter, methods of using such a catheter as well as methods of manufacturing such a catheter.

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 5 illustrates one embodiment of an intermittent urinary catheter having a plurality of small drainage openings; the catheter is illustrated in a projective view.

FIGS. 6, 7, 8, 9A and 9B illustrate the function of embodiments of an intermittent urinary catheter.

FIGS. 15, 16A and 16B illustrates embodiments of an intermittent urinary catheter.

DETAILED DESCRIPTION

Figure 1:
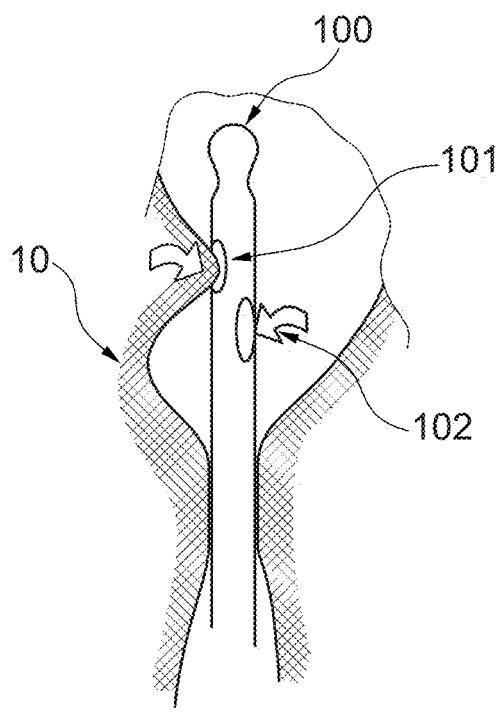
FIGS. 1 to 4 illustrate problems, which may occur with intermittent urinary catheters of the prior art.

Embodiments of the disclosure provides an intermittent hydrophilic urinary catheter defining a drainage conduit extending in a longitudinal direction from a proximal insertion end configured for insertion into a body cavity to a distal outlet end configured for draining urine from the drainage conduit, the catheter comprising a tubular portion having a tubular wall made of a substrate material and defining an inner surface towards the drainage conduit and an opposite outer surface facing away from the drainage conduit, wherein at least an insertable portion of the outer surface is covered by a layer of a hydrophilic material configured to swell by contact with a swelling medium, the hydrophilic material defining a hydrophilic surface of the catheter at a coating thickness on the outer surface, and wherein the catheter comprises a plurality of drainage openings each defined by a drainage opening wall extending between an internal opening in the inner surface and an external opening in the outer surface, wherein the drainage openings are made by laser ablation of the hydrophilic material and the substrate material such that the drainage opening wall is not covered by the hydrophilic material.

Because the drainage openings of the embodiments are made by laser ablation on the substrate material, which is covered by the hydrophilic material, the substrate material as well as the hydrophilic material is removed at the drainage openings. Therefore, there will be no remnants of hydrophilic material left at the drainage opening wall. In other words, the drainage opening wall is free from hydrophilic material. This has the effect that the drainage openings may have a very small dimension and yet not become blocked by the hydrophilic material when it swells.

Embodiments of the disclosure provides an intermittent urinary catheter defining a drainage conduit extending along a centre axis from a proximal insertion end configured for insertion into a body cavity to a distal outlet end configured for draining urine from the drainage conduit, the catheter comprising a plurality of drainage openings each extending along a centre line from an internal opening into the drainage conduit to an external opening in an outer surface, wherein at least two drainage openings have centre lines intersecting at an intersection point outside the drainage conduit.

These embodiments have the effect that the fluid flow from one single point in the bladder may flow linearly through more than one drainage opening into the drainage conduit. This may potentially provide improved flow properties and may also reduce the risk of occlusion.

Embodiments of the disclosure provides an intermittent urinary catheter defining a drainage conduit extending along a centre axis from a proximal insertion end configured for insertion into a body cavity to a distal outlet end configured for draining urine from the drainage conduit, the catheter comprising a plurality of drainage openings each extending along a corresponding centre line from an inner surface towards the drainage conduit to an outer surface facing away from the drainage conduit, wherein the drainage openings are formed in pairs such that one pair of drainage openings comprises a first drainage opening and a second drainage opening both having the same centre line.

The drainage openings are arranged on opposite sides of the centre axis. This has the effect that if the first drainage opening of the pair of drainage openings are biased against the wall of the urinary canal, there is an increased probability that the second drainage opening is not in contact with the opposite side of the urinary canal and therefore provides a more free flow of urine into the drainage conduit.

Embodiments of the disclosure provides an intermittent hydrophilic urinary catheter defining a drainage conduit extending in a longitudinal direction from a proximal insertion end configured for insertion into a body cavity to a distal outlet end configured for draining urine from the drainage conduit, the catheter comprising a tubular portion having a tubular wall made of a substrate material and defining an inner surface towards the drainage conduit and an outer surface facing away from the drainage conduit, wherein at least an insertable portion of the outer surface is covered by a layer of a hydrophilic material configured to swell by contact with a swelling medium, the hydrophilic material defining a hydrophilic surface of the catheter at a coating thickness at the outer surface, and wherein the catheter comprises a plurality of drainage openings extending between an internal opening in the inner surface and an external opening in the outer surface, and wherein the outer surface forms a projection encircling the external opening in the outer surface and extending above the hydrophilic surface when the hydrophilic material is in the non-swelled condition.

The projections will typically extend in a radial direction.

These embodiments have the effect that the risk of hydrophilic material being displaced to a position where it covers the drainage openings is limited further since it has to pass the projection.

During insertion of a urinary catheter, the tissue in the urethra may collapse into the drainage openings. Providing projections around the drainage openings may have the effect that the tissue is lifted past the drainage opening during movement of the catheter in the urethra. Thus, the projections may reduce the risk of chafing when the catheter slides along the tissue during insertion and removal.

The dimension of the projections and the thickness of the layer of hydrophilic material may be selected such that the hydrophilic material extends above the projections when the hydrophilic material is swelled. Since the hydrophilic material extends above the projections when the material is swelled, the tissue is protected by the hydrophilic material during insertion and removal of the catheter and the risk of chafing by the projections is reduced.

Embodiments of this disclosure has the effect of providing an intermittent urinary catheter with significantly reduced risk of influencing the bladder wall and ureteral tissue during intermittent catheterisation. Furthermore, the catheterization procedure of emptying the bladder will be easier, not requiring re-positioning of the catheter, thus leading to a higher probability of emptying the bladder to a satisfactory level at every catherization.

During intermittent catheterisation and emptying of the bladder, the bladder contracts and eventually the bladder wall will get close to the catheter. The pressure differential between the bladder and the external surroundings creates an outflow of urine from the bladder through the catheter. If all drainage openings in the intermittent urinary catheter are suddenly blocked by bladder wall tissue a negative pressure pulse arises in the catheter due to the moving water column of urine in the catheter abruptly being stopped. This negative pressure provides a sudden suction of tissue towards the drainage openings and, if the negative pressure is maintained, maybe even into the inner lumen of the catheter. This phenomenon will in the context of this disclosure be referred to as clogging. The suction may influence the bladder wall tissue. The magnitude of the negative pressure is dependent inter alia on the abruptness of the blockage of the drainage openings and the flow rate. If the catheter is a prior art intermittent catheter, such as one commonly provided with two drainage openings, one of the drainage openings may be clogged by bladder wall tissue which may result only in a limited negative pressure pulse, but if/when the second and last drainage opening is also clogged by bladder wall tissue, the urine flow through the catheter is abruptly stopped, resulting in a significant negative pressure pulse in the catheter. This causes the tissue in proximity of the drainage openings to be sucked into the lumen of the catheter through the drainage openings. The occurrence of this negative pressure pulse sucking the bladder tissue into the drainage openings may be what some catheter users sense as a pinch in the bladder.

Contrary to these drawbacks of commonly available catheters, the present disclosure provides an intermittent urinary catheter which uses multiple drainage openings that hinder the possibility of an abrupt closure of all drainage openings almost simultaneously, thereby eradicating the occurrence of a negative pressure pulse sucking bladder wall tissue towards and into the drainage openings. The multiple drainage openings described herein secures that during voiding, when contact between the bladder wall and catheter occurs, potential blockage of the drainage openings only takes place gradually. In addition, if the drainage openings are of a small size, it has the further advantage that when the last one of all the drainage openings is blocked by bladder wall tissue when complete voiding (no residual urine in the bladder) is reached, marginal urinal flow through that last to be blocked drainage opening is decreased to a level where abrupt closure of that last opening only causes a minor negative pressure pulse to occur.

During use of an intermittent catheter of the prior art, blocking of the drainage openings by bladder wall tissue may occur, probably due to the inflow sucking the bladder wall tissue towards the drainage opening, as described above. As documented in the tests described below and illustrated in the figures relating to prior art catheters, significant amounts of bladder wall tissue may enter into the inner lumen of the catheter and be trapped in the drainage openings due to the suction of bladder tissue. It is contemplated that this is because, the negative pressure pulse results in the drainage opening being clogged as described above and the once, the drainage opening is clogged, the pressure difference between the bladder wall and the pressure in the inner lumen gradually deforms the bladder wall such that it enters into the drainage opening. If clogging of the drainage openings reduces the urine flow remarkably or entirely, the user may then try to move the catheter up or down or rotate the catheter in order to reposition the drainage openings to regain flow. The user may also withdraw the catheter in the belief that the bladder is empty because the urine flow has stopped. The risk of influencing the bladder wall tissue due to movement of the catheter can be reduced by preventing trapping of bladder wall tissue in the drainage openings.

As described above, the contact between the bladder wall and the drainage openings of a catheter of the prior art can cause the bladder wall tissue to block the drainage openings and thereby reduce or entirely stop the urine flow. Undue blockage of the drainage openings of an intermittent catheter may lead users to withdraw the catheter in the belief that the bladder is empty since the flow has stopped or has diminished remarkably. If catheter users for this reason abort the voiding procedure prematurely, residual urine may remain in the bladder. An intermittent catheter with multiple small drainage openings according to the disclosure prevents premature blockage of the drainage openings, thereby securing urine flow until the bladder is empty. An intermittent catheter as disclosed herein with multiple drainage openings thus secures that catheter users are not falsely led to believe that the bladder is empty and thereby terminate the voiding procedure prematurely, resulting in leaving residual urine in the bladder.

In the following, whenever referring to a proximal end of an element of the disclosure, the referral is to the end adapted for insertion. Whenever referring to the distal end of an element, the referral is to the end opposite the insertion end. In other words, the proximal end is the end closest to the user, when the catheter is to be inserted and the distal end is the opposite end—the end furthest away from the user when the catheter is to be inserted.

The longitudinal direction is the direction from the distal to the proximal end. The transverse direction is the direction perpendicular to the longitudinal direction, which corresponds to the direction across the catheter.

The intermittent urinary catheter according to the disclosure comprises a main tubular portion extending from a tip portion in the proximal insertion end to a distal outlet end to the proximal end. The tubular portion can be cylindrical or conical. In embodiments, the tubular portion has an oval cross-section. The tubular portion is configured for providing urine flow through the intermittent catheter from a drainage portion to the distal end. A closed tip portion with a closed tip is positioned in the proximal end of the catheter and is provided as a rounded closed end of the tube constituting the main tubular portion of the catheter. The drainage portion of the tubular portion will typically be in the proximal portion of the tubular portion. In embodiments, the drainage portion includes multiple drainage openings providing for flow of urine between the outside of the catheter and an inside lumen of the tubular portion. In embodiments, the drainage portion is longer than the typical flow zone on a prior art catheter, where the flow zone is defined as the length from the distal edge of the distal eyelet to the proximal edge of the proximal eyelet. In embodiments, the intermittent catheter comprises a connector in the distal end. In an embodiment the connector comprises a flared end of the catheter so that the diameter of the connector increases with respect to the tubular portion. In embodiments, the intermittent catheter comprises a handle in the distal end, which has a length allowing the user to manipulate the catheter.

Usually intermittent urinary catheters are from size 8 FR to size 18 FR. FR (or French size or Charriere (Ch)) is a standard gauge for catheters approximately corresponding to the outer circumference in mm. More accurately, the outer diameter of the catheter in mm corresponds to FR divided by 3. Thus 8 FR corresponds to a catheter with an outer diameter of 2.7 mm and 18 FR corresponds to a catheter with an outer diameter of 6 mm.

The hydrophilic coating may be provided only on the insertable part of the catheter. The hydrophilic surface coating is of the kind which, when hydrated or swelled using a swelling medium, reduces the friction on the surface area of the catheter which is intended to be inserted into the lower urinary tract of a user corresponding to the insertable part of the catheter.

An intermittent hydrophilic catheter differs from an indwelling catheter in that the hydrophilic surface coating of such a catheter is not suitable for indwelling use, because the surface coating tends to stick inside the mucosa of the urethra if left inside the body for a period exceeding 5-20 minutes, due to the hydrophilic coating transforming from being highly lubricious when fully wetted (95% weight water) to being adhesive when the hydration level of the coating is reduced (<75% weight water).

The catheter may have a closed tip at the proximal insertion end, and it may, in particular, have a plurality of draining openings distributed over a portion of the catheter located near the closed tip, e.g. constituting half or one third of the entire length of the catheter measured from the proximal end to the distal end.

The drainage openings described herein are sometimes in the art referred to as eyelets or eyes. The drainage openings have a closed loop circumference and may be circular, oval, square, triangular and any other closed loop shape. This closed loop shape defines the external opening of the drainage opening. The internal opening of the drainage opening will also have a closed loop circumference and will typically, but not necessarily have the same shape as the external opening of the drainage opening.

The catheter may have at least 12 draining openings, and the draining openings may particularly be arranged in one or more groups, e.g. in straight rows extending in the longitudinal direction. The drainage openings ay also be arranged in groups such that the denseness of the drainage openings between the groups differs.

Each drainage opening may be defined by a wall extending from an internal opening in an inner surface towards the drainage conduit to an external opening in an outer surface facing away from the drainage conduit. Thus, the drainage opening wall may have a height corresponding to the distance between the inner surface and the outer surface of the tubular portion of the catheter. The drainage opening walls may particularly extend continuously between the inner surface and the outer surface. The internal opening may also be known as the outlet opening and the external opening may also be known as the inlet opening.

The tubular wall of the tube may have a uniform wall thickness thereby providing a uniform length of the drainage openings.

The tubular portion has a uniform outer surface thereby enabling a uniform bonding with the hydrophilic material. Furthermore, the risk of displacement of the hydrophilic material and thereby potentially blocking of the drainage openings is minimised.

Embodiments relate to a catheter provided with a closed tip in the proximal insertion end. The closed tip could be formed as a Nelaton tip, a flex tip, or generally as a tip of the kind known for urinary catheters.

In the context of this disclosure a body cavity refers to a urethra.

The catheter may define a non-drainage part distally of the tip and a drainage part distally of the non-drainage part, the drainage part being provided with the plurality of drainage openings. The non-drainage part may e.g. constitute less than 3 cm., or less than 2 cm or less than 1 cm. and the drainage part may constitute less than 20 cm or less than 15 cm or less than 10 cm.

The inflow of urine through the multiple drainage openings depends on the total sum of the cross-sectional area of all of the drainage openings (the total inflow area) and the pressure gradient between the drainage openings and the outlet from the catheter at the distal end, as explained above. The total sum of cross-sectional area of the multiple drainage openings (the total inflow area) has to be large enough to provide for an adequate inflow of urine, otherwise emptying of the bladder would take too long and thus be an inconvenience to the user of the intermittent catheter. Each drainage opening provides a certain resistance to inflow of urine, which resistance depends inter cilia on the cross-sectional area of the drainage opening and the thickness of the catheter material at the drainage opening, i.e. the extension of the drainage opening wall from the internal opening to the external opening.

Embodiments relate to the total sum of the cross-sectional area of the multiple drainage openings being larger than the cross-sectional area of the drainage conduit of the catheter just distally of the drainage openings. By just distally of the drainage openings is meant within 5 mm in longitudinal distal direction from the most distal drainage opening.

Embodiments relate to the tubular portion defining a convex outer surface, and wherein the total inflow area of the drainage openings in the convex outside surface of the tubular portion is larger than a cross-sectional area of the drainage conduit of the catheter in a cross section perpendicular to a longitudinal direction of the tubular portion at a position distally of the drainage openings.

In an embodiment, the total sum of the cross-sectional area of the multiple drainage openings (the total inflow area) is larger than twice the cross-sectional area of the inside lumen of the catheter just distally of the drainage openings. The total inflow area of the drainage openings is provided in a convex outside surface of the tubular portion. Providing such a large total inflow area ensures that the resistance of flow at the drainage openings will not hinder a filling of the drainage conduit of the catheter. Therefore, the inflow through the drainage openings into the drainage conduit does not limit the flow through the intermittent catheter.

Further embodiments relate to the total sum of the cross-sectional area of the multiple drainage openings (the total inflow area) being at least three times larger than the cross-sectional area of the drainage conduit of the catheter.

Embodiments relating to the total inflow area in a convex outside surface of the tubular portion being at least equal to or higher than the cross-sectional area of the drainage conduit of the tubular portion may relate to a catheter having a cylindrical tubular portion. In this case, the cross-sectional area of the drainage conduit is constant through-out the length of the catheter. However, these embodiments may also relate to a catheter having a conical tubular portion. In this case, the cross-sectional area increases along the length. In this case, the total inflow area should be compared to the cross-sectional area of the drainage conduit just distally of the most distal drainage openings, i.e. within 5 mm in the distal direction of the most distal drainage opening.

Embodiments relate to the number of drainage openings being higher than required for filling the drainage conduit just distally of the drainage openings. This is to be understood such that, depending on the size of the individual drainage openings, a certain number of drainage openings is required to provide a total inflow area corresponding to the cross-sectional area of the drainage conduit distally of the drainage openings. This number of drainage openings is in this disclosure referred to as first predetermined number of drainage openings. Thus, embodiments relate to the number of drainage openings being higher than a first predetermined number of drainage openings.

Embodiments relate to an intermittent urinary catheter as defined above and provided with multiple drainage openings configured for providing a total inflow area exceeding the cross-sectional area of the drainage conduit in the catheter just distally of the most distal of the drainage openings.

When the total inflow area exceeds the cross-sectional area of the drainage conduit of the catheter or the number of drainage openings is higher than what is required for filling the drainage conduit, then it is ensured that at least one drainage opening is always available for providing inflow. This is because the inflow is less than what the drainage openings are able to drain—and therefore at least one drainage opening will be able to provide further inflow, should another one of the drainage openings being contemporarily blocked by bladder tissue. This means that the flow through the catheter will be continuous until the bladder is empty. Thereby the risk of leaving residual urine in the bladder is substantially alleviated.

In the context of this disclosure, pressure means partial pressure, not absolute pressure. This means that the pressure is always indicated as a pressure difference between the point of measurement and the ambient pressure.

In an embodiment, the largest dimension of an individual drainage opening in an outer convex surface of the tubular portion is less than 1 mm. By largest dimension is meant a diameter in case of a circular drainage opening, the major axis in case of ellipse, the diagonal in case of a rectangular or square opening and so forth. In other words, the largest dimension means the largest of the dimensions across the opening between two oppositely located points on the perimeter of the opening at an outer convex surface of the tubular portion. In a related embodiment, each of the drainage openings has a cross-sectional area of less than 0.8 mm$^2$.

Thereby, it is secured that a negative pressure no larger than 50 mBar when measured under 10 cm $H_2O$ can occur, thus the influence to the bladder wall tissue is significantly reduced as compared to prior art catheters having a few (such as two) large drainage openings.

In an embodiment, the largest dimension of any one individual drainage opening in an outer convex surface of the tubular portion is less than 0.7 mm. In a related embodiment, each of the individual drainage openings has a cross-sectional area of less than 0.4 mm$^2$. Thereby, it is secured that the negative pressure can be no more than 40 mBar when measured under 10 cm $H_2O$.

In an embodiment, the largest dimension of any one individual drainage opening in an outer convex surface of the tubular portion is less than 0.5 mm. In a related embodiment, each of the individual drainage openings has a cross-sectional area of less than 0.2 mm$^2$.

In an embodiment, the number of drainage openings are more than 20.

Thereby, the likelihood of all drainage openings being blocked at once is significantly reduced.

In embodiments, the number of drainage openings can be significantly higher, for example more than 200 or even around 260 drainage openings. The number can also be around 100, 120 or 150—or close to 200 such as 180.

Embodiments relate to an intermittent urinary catheter wherein the catheter is a CH10, each drainage opening has largest dimension in an outer convex surface of the tubular portion of approximately 0.4 mm, and the number of drainage openings is larger than 32. Such a catheter provides for adequate inflow into the lumen of the catheter such that each drainage opening contributes to the draining, but at least one drainage opening is always left open. By approximately 0.4 mm is meant between 0.35 and 0.45 mm.

Other embodiments relate to an intermittent urinary catheter, wherein the catheter is a CH12, each drainage opening has largest dimension in an outer convex surface of the tubular portion of approximately 0.7 mm, and the number of drainage openings is larger than 15. By approximately 0.7 mm is meant between 0.65 mm and 0.75 mm.

Embodiments relate to an intermittent urinary catheter as in any of the preceding claims, wherein each one of the drainage openings extends transversely to a longitudinal direction of the catheter. By extending transversely is meant that a central axis of the drainage opening is substantially perpendicular to the longitudinal axis of the catheter meaning within 20 degrees in either direction.

In an embodiment, the drainage portion has a length of 4 cm in a longitudinal direction of the intermittent catheter. This provides for good emptying of the bladder. The drainage portion is positioned distally of the closed tip portion, thus if the closed tip portion is less than 2 cm in a longitudinal direction, the drainage portion is within the most-proximal 6 cm of the catheter. This is a common insertion length of intermittent catheters into a bladder—thus having the drainage portion positioned inside the bladder provides for a large cross-sectional area of the multiple drainage openings being inside the bladder and hence a good and fast draining of the bladder. A drainage portion of approximately 4 cm may be useful for both male and female catheters. By approximately 4 cm is meant between 35 mm and 45 mm, such as 40 mm, 37 mm or 42 mm.

In an embodiment, the drainage portion has a length of 10 cm in a longitudinal direction of the intermittent catheter. This provides an enhanced security for emptying of the bladder as there will be drainage openings positioned in the lower part of the bladder, at the bladder neck. Typically, the intermittent catheter will be inserted 5-6 cm into the bladder, thus in these embodiments the drainage part will extend into a portion of the urethra as well as being in the bladder. A catheter with a drainage portion of 10 cm or more is particularly useful for male catheters. Other embodiments relate to a drainage portion having a length of approximately 8 cm, meaning between 75 mm and 85 mm, such as 77 mm, 80 mm or 82 mm.

In an embodiment, the drainage portion has a length of 15 cm in a longitudinal direction of the intermittent catheter. This provides an enhanced security for emptying of the bladder. This is particularly beneficiary for users who have a tendency of inserting their intermittent catheter too far into the bladder, probably because they have no sense of feeling during insertion of the catheter.

Embodiments relate to a drainage portion having a length of approximately 2 cm, meaning between 15 and 25 mm. Such a short drainage portion is particularly useful for female catheters, where the urethra is quite short. A short drainage portion reduces the risk of urine flowing out through the drainage openings, in case some of the drainage openings are situated outside the urethra.

In an embodiment, the drainage openings are positioned scattered in the longitudinal direction as well as around the circumference of the catheter.

In an embodiment, the drainage openings are positioned in four longitudinal rows with 90 degrees between them around the circumference.

In an embodiment, the drainage openings are positioned in 6 longitudinal rows with 60 degrees between them around the circumference.

In an embodiment, the drainage openings are positioned in 8 longitudinal rows with 45 degrees between them around the circumference.

In an embodiment, the drainage openings are positioned in two longitudinal rows with 180 degrees between them around the circumference.

In an embodiment, the drainage openings are positioned in two pairs of parallel rows with 180 degrees between the rows around the circumference.

In an embodiment, the drainage openings are helically dispersed around the circumference.

An increased number of directions provide for better inflow and decreased risk of bladder tissue blocking contact with all drainage openings.

In an embodiment, the tip portion of the catheter is a nelaton tip, where the proximal end is simply closed off providing a half-spherical closed end.

The tip portion may be integrally moulded with the main tubular part—either as 1 component or 2 component moulding—or it may be provided as a separate element and then attached to the main tubular part, e.g. by welding or adhering.

In an embodiment, the tip portion mis a flex tip. In this type of embodiment, the tip of the urinary catheter comprises, from the distal end of the tip portion, a drainage part with drainage openings for letting urine into the inner lumen of the catheter, an intermediate part, where the catheter diameter is decreased with respect to the diameter of the remaining part of the catheter, and a proximal part having a bulb with a diameter close to or exceeding the diameter of the tubular part of the catheter. The bulb may also have a diameter that is slightly less than the diameter of the tubular part of the catheter. The bulb may be close to spherical in shape or may be slightly elongated and shaped as an olive or droplet. This type of tip portion may be useful for male users to guide the catheter around the bend in the urethra at the prostate.

The substrate material may be a polyurethane material (PU) or polyvinyl chloride (PVC) or poly-olefins such as a polyethylene (PE). Other materials may be silicone materials, latex material, styrenic block copolymers, TPS (TPE-s) (thermoplastic elastomeric materials), thermoplastic vulcanizates, TPV, Thermoplastic copolyester, TPC (TPE-E), thermoplastic polyamides, TPA, (TPE-A). The substrate material may also be known as the base material. The hydrophilic material could be Polyvinylpyrrolidone (PVP) and Copolymers.

The drainage openings may be formed in pairs such that one pair of drainage openings comprises a first drainage opening and a second drainage opening both having the same centre line.

Embodiments relate to the pairs of drainage openings being located with an oblique angle with respect to the longitudinal axis. Embodiments relate to the pairs of drainage openings being located with an angle of between 80 and 87 degrees with respect to the longitudinal axis, such as an angle between 85 and 87 degrees.

The drainage openings may be shaped such that the wall of the first drainage opening converges in a direction from the external opening to the internal opening and the wall of the second drainage opening diverges in the direction from the external opening to the internal opening.

By converging is herein meant that the distance between wall portions on opposite sides of the centre line is reduced in the direction from the outer surface to the inner surface. In other words, the external opening has a larger area than the internal opening. By diverging is herein meant that the distance between wall portions on opposite sides of the centre line increases in the direction from the outer surface to the inner surface. In other words, the external opening has a smaller area than the internal opening.

If the drainage opening is circular, the drainage opening wall may have the shape of a truncated cone. Herein, we refer to the shape being truncated-cone-like to denote that the cross section of the drainage opening need not to be circular.

The converging and diverging walls of the pair of drainage openings provides different flow characteristics though the first and the second drainage opening and increases the likelihood of one of the two drainage openings being open if the other one should be blocked. The specific characteristic shape of the diverging and converging wall makes the external opening in the outer surface bigger than the internal opening in the inner surface for one of the drainage openings and opposite for the other one of the drainage openings of the pair of drainage openings. Accordingly, blocking tissue contact with a relatively large opening may not prevent flow through a relatively small opening vice versa.

The first drainage opening, and the second drainage opening may have different dimensions. I.e. the dimension of the first drainage opening in a cross-section transverse to the centre line may be different from the dimension of the second drainage opening, particularly when comparing the dimension in cross sections having the same distance to the inner and outer surfaces.

The coating thickness may decrease towards each inlet opening in the outer surface to thereby reduce the risk of blocking the flow through the inlet opening when the hydrophilic material swells. This means that the coating is thicker in areas between the drainage openings than in areas close to the drainage openings. By close to the drainage openings is meant within a distance of 0.5 mm from an edge of the drainage opening.

The tubular portion has a uniform outer surface thereby enabling a uniform bonding with the hydrophilic material and further avoiding displacement of the hydrophilic material and thereby potentially blocking of the drainage openings.

The disclosure provides methods of manufacturing. As an example, the laser ablation can be made by using a $CO_2$-laser.

The disclosure provides a method of making a hydrophilic urinary catheter, the method comprising providing a tube, e.g. by extruding a substrate material through a die which defines a tubular shape with an inner surface towards a drainage conduit and an opposite outer surface facing away from the drainage conduit, coating the outer surface with a hydrophilic material to define a hydrophilic surface, and providing a plurality of drainage openings from the outer surface to the inner surface by laser ablation of the hydrophilic material and the substrate material such that drainage opening walls extending between the inner surface and the outer surface are uncoated. The laser ablation is thereby used not only to establish the drainage openings but also to remove hydrophilic material and thereby reduce the risk of blocking the drainage openings with hydrophilic material.

The disclosure further provides a method of making a hydrophilic urinary catheter. According to the method, a tube is provided by extruding a substrate material through a die which defines a tubular shape with an inner surface towards a drainage conduit and an opposite outer surface facing away from the drainage conduit. The outer surface is coated with a hydrophilic material to define a hydrophilic surface, and subsequently, i.e. after the coating of the outer surface, a plurality of drainage openings is provided from the outer surface to the inner surface by laser ablation of the hydrophilic material and the substrate material such that drainage opening walls extending between the inner surface and the outer surface are uncoated.

By this process, hydrophilic material in the drainage openings are avoided without increasing the complexity of the manufacturing, and the method therefore provides an easy way of producing a catheter with improved qualities and potentially without increasing manufacturing costs.

Embodiments relate to method of making an intermittent urinary catheter, the method comprising providing a tube made from a substrate material and defining a tubular shape with an inner surface towards an internal drainage conduit and an opposite outer surface facing away from the internal drainage conduit, and providing a plurality of drainage openings extending between internal openings in the inner surface and external openings in the outer surface by laser ablation of the substrate material, wherein the laser ablation is carried out with laser light emitted from an emitter point outside the drainage conduit at an emission angle such that a first group of drainage openings is provided with a first emission angle and a second group of drainage openings is provided with a second emission angle.

This method may provide an efficient manufacturing allowing a plurality of drainage openings to be made from one and the same point of origin, e.g. by laser ablation from a single emission point.

The drainage openings may be provided in pairs of one drainage opening from the first group of drainage openings and one drainage opening from the second group of drainage openings and where the emitter point is moved relative to the tubular portion between each pair of drainage openings.

The distance from the emitter point to the outer surface may be maintained constant when providing the drainage openings.

The drainage openings may be provided by ablation while a pressure in the drainage conduit is changed relative to a pressure outside the drainage conduit.

Embodiments relate to a method of making a hydrophilic urinary catheter, the method comprising providing a tube made from a substrate material and defining a drainage conduit extending along a centre axis from a proximal insertion end configured for insertion into a body cavity to a distal outlet end configured for draining urine from the drainage conduit, and providing a plurality of drainage openings extending between internal openings in an inner surface towards the drainage conduit and external openings in an outer surface facing away from the drainage conduit, the drainage openings being made by laser ablation of the substrate material, wherein the laser ablation is carried out to form pairs of drainage openings comprising a first drainage opening and a second drainage opening provided by simultaneous ablation of the substrate material along a common centre line on opposite sides of the centre axis.

The laser light may particularly be emitted from an emitter point outside the drainage conduit through the internal drainage conduit. The emitter point may be at a distance from the outer surface corresponding at least to 10 times the distance from the outer surface to the centre axis or corresponding at least to 15 or 20 times the distance from the outer surface to the centre axis.

The drainage openings may be provided by ablation while a pressure in the drainage conduit is changed relative to a pressure outside the drainage conduit.

The laser light may be emitted in at least two subsequent pulses, e.g. in 3, 4, 5, 6 or more subsequent pulses. The pulses may particularly be emitted with a frequency above 1 Hz, e.g. above 2, 3, 4, 5, 6 or even a higher number of Hz.

The method may include the step of determining, for at least one of the first and second drainage opening, a hole size. In this way, the laser ablation may be carried out in a number of shots determined by the hole size. In one embodiment, a limit size is defined, and the number of shots is increased until the limit size for at least one of the first and second drainage openings is reached. In one embodiment, a limit size is defined for both the first and the second drainage opening, and the number of shots is increased until both drainage openings have the required size.

Herein, the term:

"continuous" defines that the surface in question extends continuously with no sharp pointed corners or edges or similar distinct geometrical changes defining a radius of curvature being less than 3 millimetre.

"uniform outer surface" defines as an addition to the surface being continuous that the outer surface has the same surface texture, colour, and/or roughness or slipperiness.

"intermittent" defines that the catheter is not for indwelling use, and that it comprises no balloon or other means for fixation in the bladder.

"hydrophilic" defines that the material swells to a degree where the resulting hydro gel reduces the surface friction and facilitates an easier insertion of the proximal end into the body cavity of the user.

EXAMPLES

Figure 32:
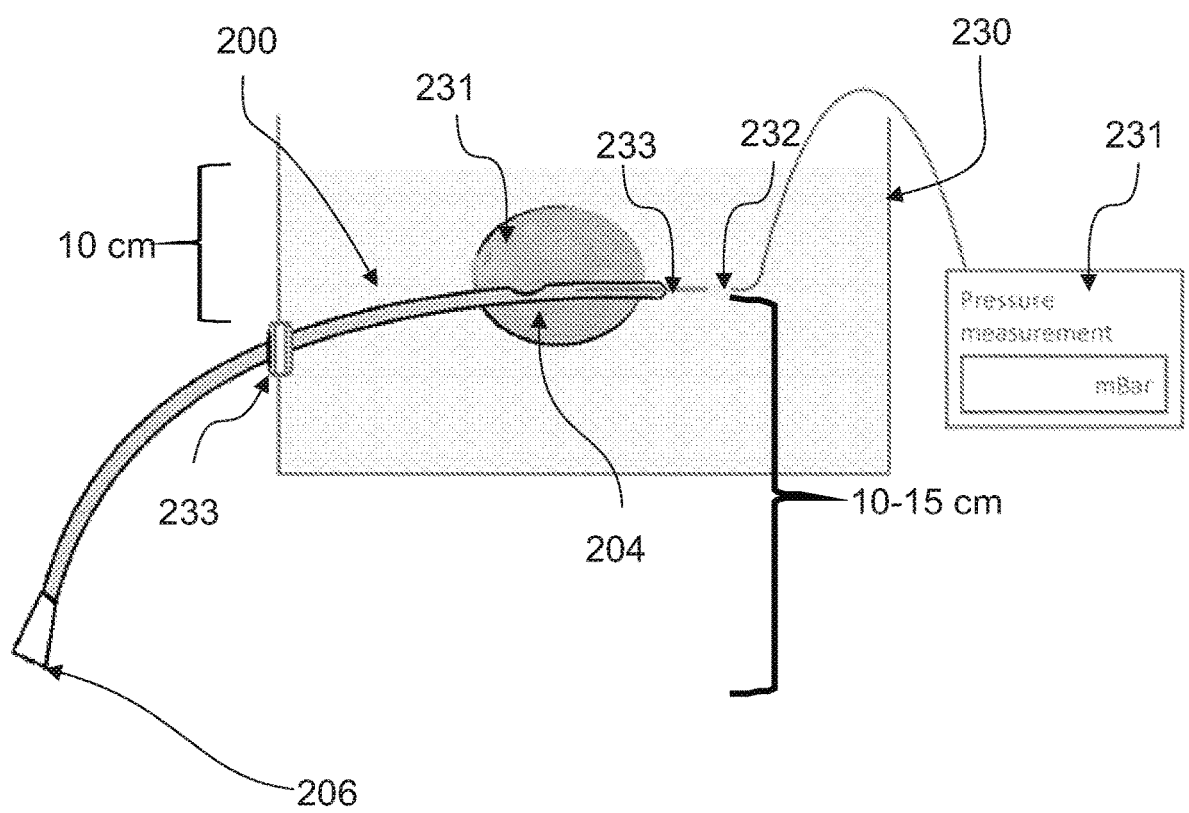
FIGS. 32 to 34 illustrate test set-ups used to determine a pressure pulse in an intermittent urinary catheter.
Figure 33:
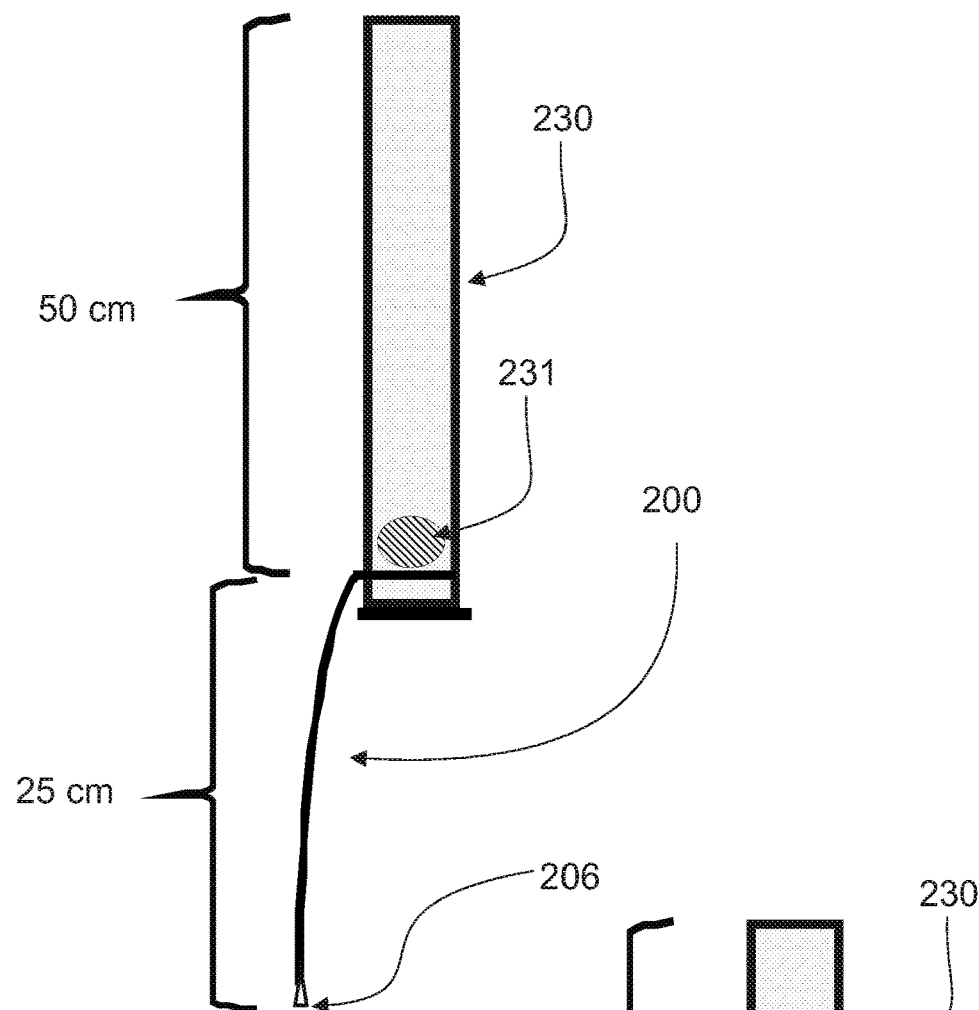
Figure 34:
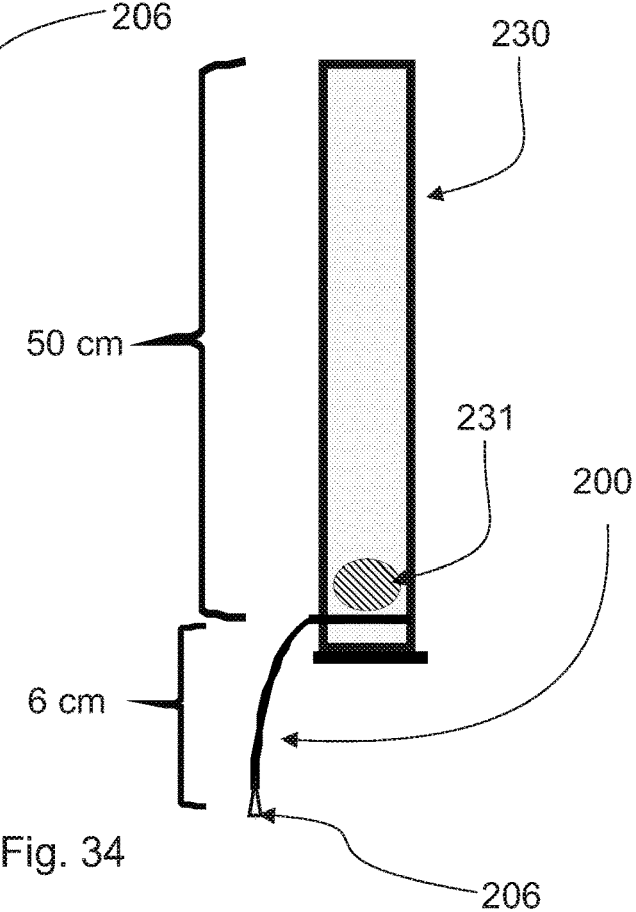

The first tests were performed to compare the level of a pressure pulse between prior art catheters and catheters having small drainage openings with a largest dimension below 1.2 mm. The aim of these first tests is to simulate the situation, where one drainage opening becomes blocked by bladder tissue and the second (last) drainage opening suddenly becomes blocked. Catheters having one small drainage opening (largest dimension below 1.2 mm) were used and compared to a standard prior art catheter provided with two standard sized drainage openings. In the latter case, one drainage opening was prior to testing blocked by a piece of tape. In all tests, the catheter was submerged in a water tank and draining initiated. The test set-up is shown in FIGS. 32 to 34 and mentioned below. The pressure pulse in the inner lumen of the catheter was determined at the moment of blocking the second drainage opening. This corresponds to the situation during a catheterisation, where a first one of the two drainage openings in a prior art catheter is blocked either by bladder tissue or by urethral tissue and the suction through the catheter (caused by the flowing liquid) suddenly provides a blockage also of the second one of the two drainage openings by tissue.

The equipment used for the test is listed here:
Water tank with hole and O-ring
25 L of water
Catheter with one open drainage opening. If the catheter is provided with two drainage openings, one drainage opening was blocked during the test.
Waterproof pressure sensor attached to needle
5×5 cm piece of porcine bladder
Latex gloves
The testing was done according to the following test-protocol:
provide a water tank including a sealing adapted for providing a liquid tight sealing around the circumference of a catheter
Insert the catheter tip into the tank through the liquid-tight sealing, until the one open drainage opening is well inside the water tank
Let the water begin to flow out through the catheter
Make sure that there are no air bobbles in the catheter by tapping it
Insert the sensor-needle into the catheter lumen app. 1 cm from the one open drainage opening
Make sure that there are no air bubbles in the catheter or in the needle. This is important as even small water bubbles can obscure the pressure readings
Once there are no air bubbles in the catheter or in the needle, adjust the catheter's position in the water to an immersion depth of 10 cm, meaning that the one open drainage opening is approximately 10 cm below the surface of the water
Position the portion of the catheter external to the water tank so that the height difference between the one open drainage opening and the catheter connector is around 15-20 cm.
Put on latex gloves, and take the porcine bladder tissue
Submerge the tissue in the water
Start the pressure recording, and make sure to tare the sensor, i.e. set it to zero
Slowly guide the porcine bladder tissue towards the one open drainage opening When the porcine bladder tissue encounters the one open drainage opening, a large (negative) pressure fluctuation occurs in the inner lumen of the catheter Note the magnitude of this pressure fluctuation The pressure fluctuation noted corresponds to the pressure pulse in the lumen of the catheter. It will be noted as a (negative) peak on the pressure curve—see examples in FIG. 26-28.

Some test results are shown in Table 1 below:

TABLE 1

| ID  | Largest dimension (mm) | Suction pressure (mBar) |
|-----|------------------------|-------------------------|
| 1.1 | 0.20                   | −1                      |
| 1.2 | 0.46                   | −8                      |
| 1.3 | 0.55                   | −15                     |
| 1.4 | 0.65                   | −15                     |
| 1.5 | 0.97                   | −44                     |
| 1.6 | 3.90                   | −200                    |

As can be seen from the table above, when the largest dimension of a drainage opening is below 1 mm (ID 1.1-1.5), the suction pressure is significantly reduced compared to a prior art catheter with a drainage opening having a largest dimension of 3.9 mm (ID 1.6). Embodiments of catheters according to the disclosure as in ID 1.1 to 1.5 of Table 1, all have a suction pressure below 50 mBar (below 44 mBar), whereas the prior art catheter in ID 1.6 with a drainage opening having a largest dimension of 3.9 mm has a suction pressure of 200 mBar. Thus a threshold value of suction pressure in a lumen of an intermittent catheter according to this disclosure may be set to 50 mBar, when tested under 10 cm H$_2$O as described above in Example 1.

Figure 26:
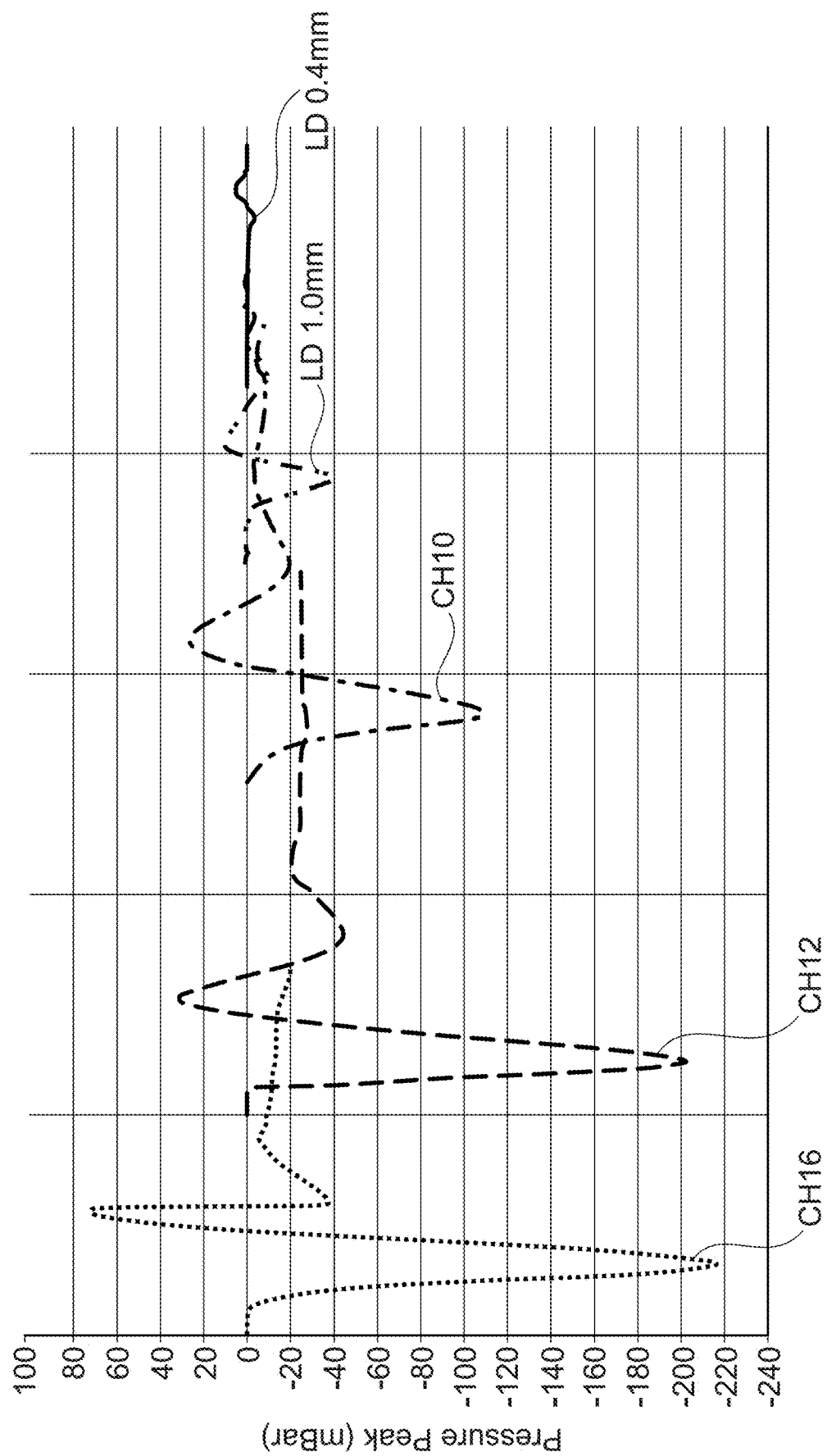
FIGS. 26 to 28 illustrate the magnitude of pressure pulses in an intermittent urinary catheter.
Figure 29A:
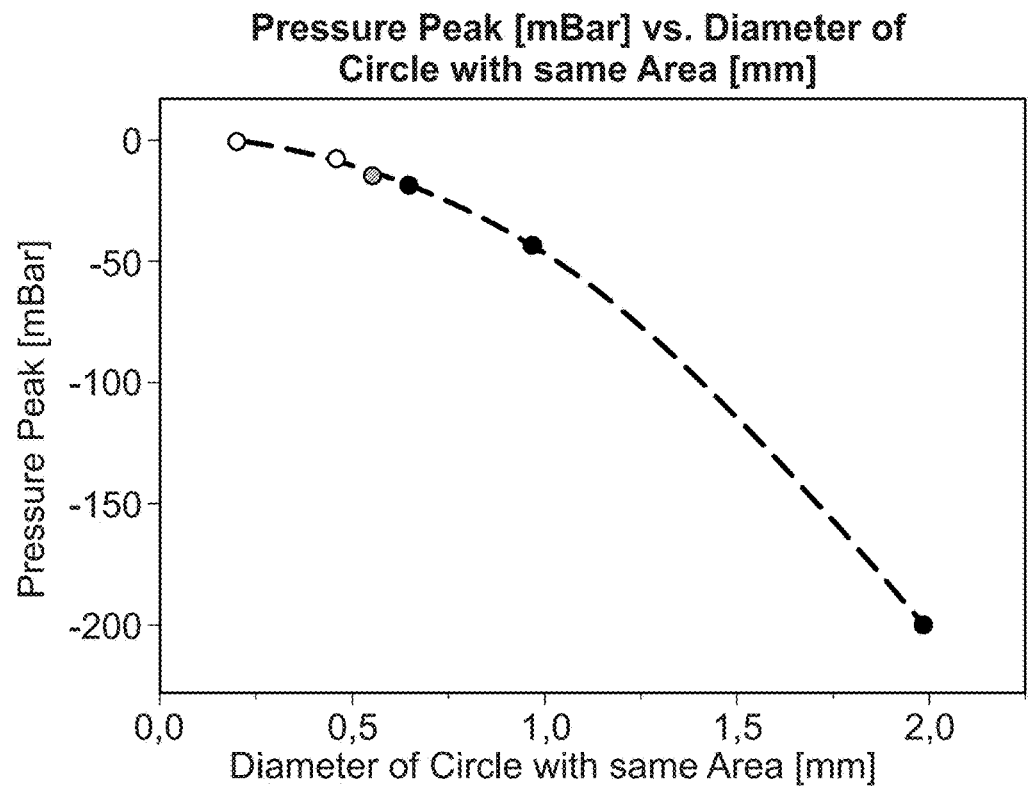
FIGS. 29A, 29B, 30 and 31 illustrates the pressure pulse as a function of the size of the drainage openings.
Figure 29B:
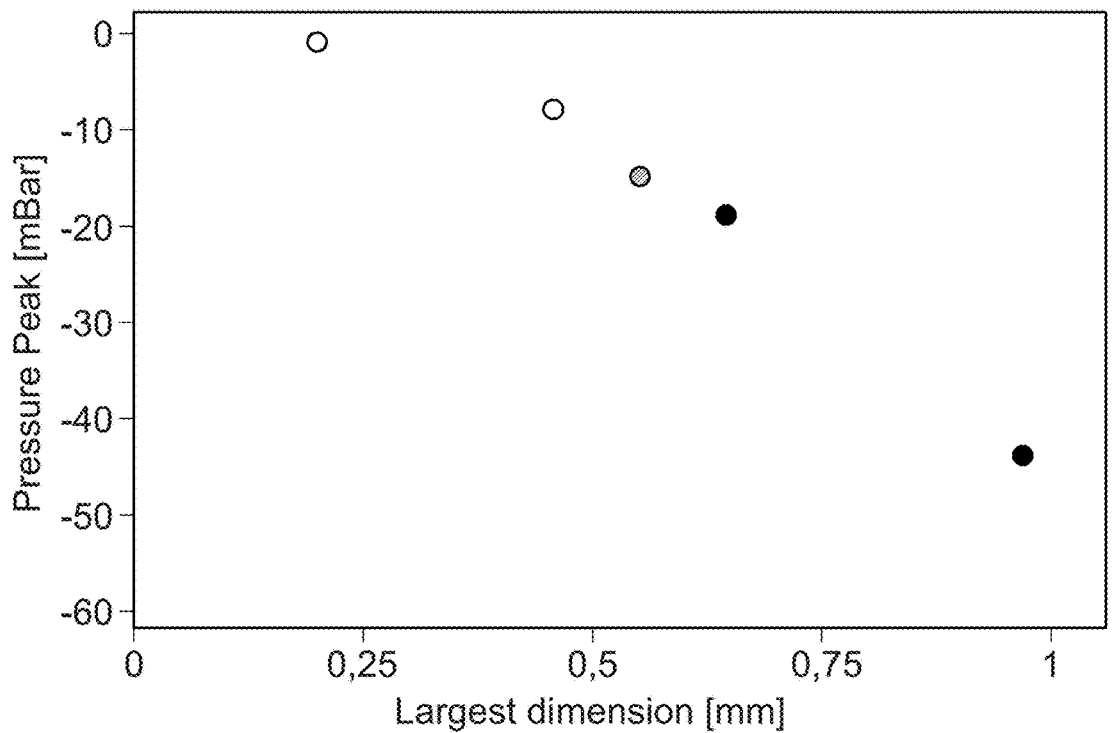

The test results are also illustrated in FIGS. 26, 29A, 29B.

The pressure inside a normal functioning bladder may reach around 400-500 mBar (40-50 cm H$_2$O) prior to emptying.

The second and third tests was done in a similar fashion—the only difference being that the catheter was submerged under 50 cm of H$_2$O as opposed to 10 cm. Furthermore, both male and female catheters were tested. The male catheters were tested with a height difference of 25 cm between the drainage opening and the outlet (the connector) and the female catheters were tested with a height difference of 6 cm between the drainage opening and the outlet (the connector).

Results are shown in Table 2 and Table 3 below:

TABLE 2

| ID   | Largest dimension (mm) | Suction pressure (mBar) |
|------|------------------------|-------------------------|
| 1.7  | 0.19                   | −15                     |
| 1.8  | 0.32                   | −55                     |
| 1.9  | 0.40                   | −86                     |
| 1.10 | 0.51                   | −125                    |
| 1.11 | 0.60                   | −166                    |
| 1.12 | 0.87                   | −300                    |
| 1.13 | 0.99                   | −354                    |
| 1.14 | 4.00                   | −652                    |

TABLE 3

| ID | Largest dimension (mm) | Suction pressure (mBar) |
| --- | --- | --- |
| 1.15 | 0.19 | −12 |
| 1.16 | 0.32 | −48 |
| 1.17 | 0.40 | −72 |
| 1.18 | 0.51 | −100 |
| 1.19 | 0.60 | −128 |
| 1.20 | 0.87 | −233 |
| 1.21 | 0.99 | −304 |
| 1.22 | 4.00 | −639 |

Results are also shown in FIGS. 27, 28, 30 and 31. ID 1.7-1.14 have been tested on male catheters and 1.15-1.22 were tested on female catheters.

The catheters tested as ID 1.7-1.13 and 1.15-1.21 were Polyurethane catheters of the type marketed by Coloplast A/S under the brand name "SpeediCath®"-catheters, whereas the prior art catheter (ID 1.14 and ID 1.22) tested were PVC grade catheters marketed by Hollister Inc under the brand name "VaPro®"-catheters. All types of catheters were of size CH12. In the SpeediCath® catheters (ID 1.7-1.13 and ID 1.15-1.22) only one drainage opening was made by laser cutting and in the catheters of ID 1.14 and ID 1.22, one of the two existing drainage openings was blocked prior to testing, as described above.

It is preferable, if the suction pressure at all times is below the pressure reached inside a normal functioning bladder. And in particular, suction pressures of approximately half of the level of a prior art catheter is an improvement. Thus, embodiments relate to an intermittent urinary catheter having drainage openings and being configured for providing a pressure pulse below a threshold value of 350 mBar when tested as described in Example 1, with the modification that the immersion depth is 50 cm and the height difference between the drainage opening and the outlet is 25 cm. Further embodiments relate to an intermittent urinary catheter having drainage openings and being configured for providing a pressure pulse below a threshold value of 300 mBar when tested as described in Example 1, with the modification that the immersion depth is 50 cm and the height difference between the drainage opening and the outlet is 6 cm. Related embodiments relate to an intermittent urinary catheter having drainage openings and being configured for providing a pressure pulse below a threshold value of 200 mBar. Related embodiments relate to an intermittent urinary catheter having drainage openings and being configured for providing a pressure pulse below a threshold value of 100 mBar.

Another test was performed to evaluate the number of drainage openings needed for providing an optimal flow rate through an intermittent catheter according to the disclosure. In this test, 108 prototype catheters were made and the flow through each catheter was determined. The 108 catheters were in three CH sizes, CH10, CH12 and CH16. The catheters were provided with drainage openings of three sizes, a diameter of 0.4 mm, a diameter of 0.6 mm and a diameter of 0.8 mm. The number of drainage openings were varied between 15 and 240 as was the positioning of the drainage openings in rows, which was varied between 3 and 6 rows.

Figure 35:
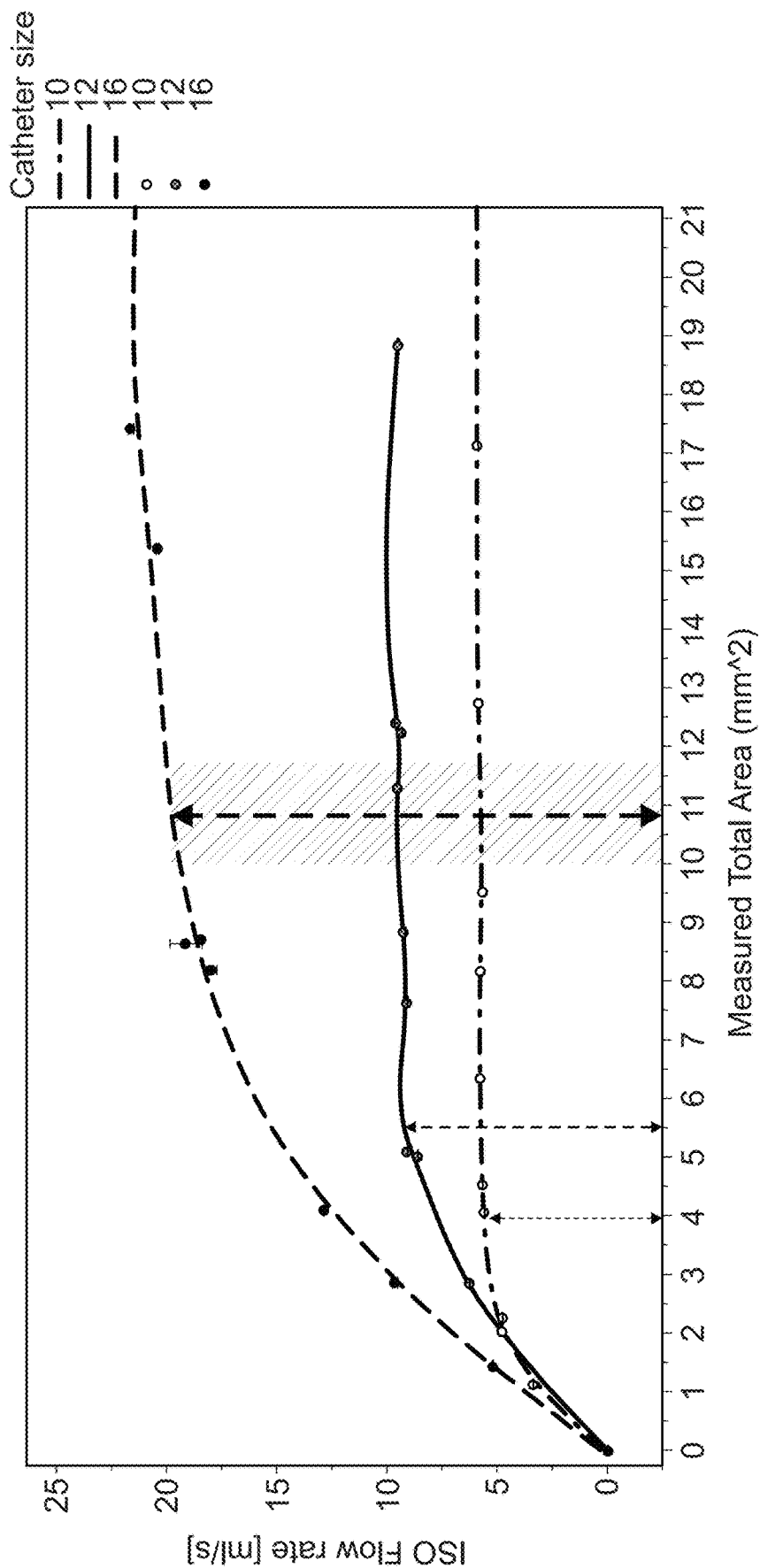
FIG. 35 illustrate a curve of the flow rate as a function of the total inflow area.

The results are illustrated in Table 4 below as well as in FIG. 35.

TABLE 4

| Size of catheter | Cross-sectional area of inside lumen (mm²) | Sum of cross-sectional area of drainage openings needed for flow-convergence (mm²) |
| --- | --- | --- |
| CH10 | 3.98 | 4 |
| CH12 | 5.52 | 5.5 |
| CH16 | 11.05 | 11 |

The results indicate, that when the total sum of the cross-sectional area of the drainage openings (the total inflow area) reaches the level of the cross-sectional area of the inner lumen of the catheter, then the flow-rate through the catheter does not increase any further. In other words, the flow converges when the total inflow area reaches the level of the cross-sectional area of the inner lumen.

DETAILED DESCRIPTION OF THE DRAWING

Embodiments, and features of the various exemplary embodiments described in this application, may be combined with each other ("mixed and matched"), unless specifically noted otherwise.

Figure 2:
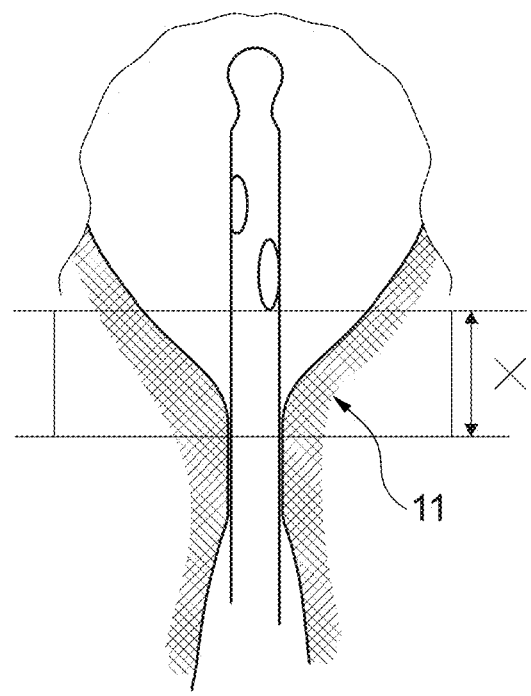
Figure 3:
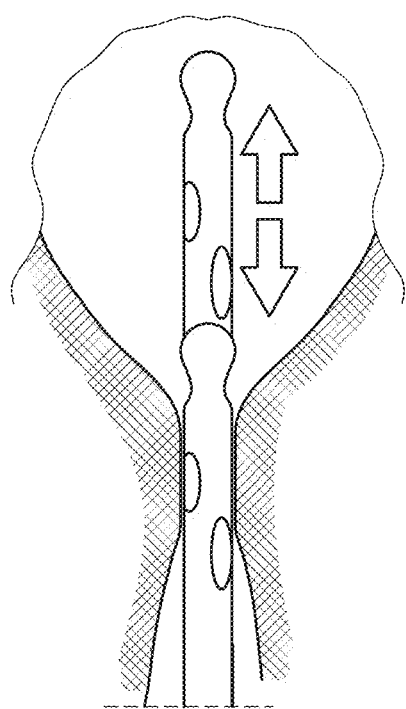
Figure 4:
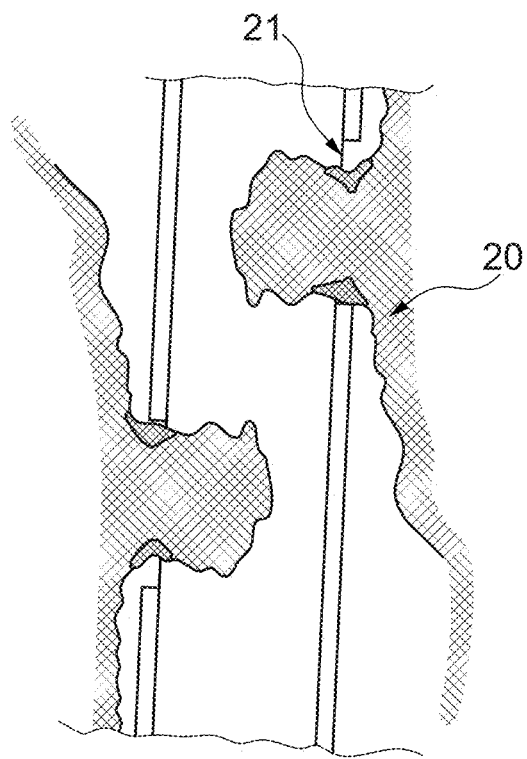

FIGS. 1-4 illustrate various issues with prior art catheters. FIG. 1 illustrates a part of a prior art catheter 100 having two drainage openings 101, 102 inserted into the bladder 10. During catheterisation, one drainage opening 101 may be blocked by the bladder wall tissue as illustrated, and then all draining of urine from the bladder occurs through the second drainage opening 102. This situation creates a high suction effect through the second drainage opening 102, which may cause bladder wall tissue to enter into contact with this second drainage opening 102, as described above. FIG. 2 illustrates a part of a prior art catheter 100 situated in the bladder 10. This figure illustrates a situation in which the prior art catheter sits too high in the bladder 10, i.e. above the bladder neck 11 and thus the bladder 10 will not empty completely during catheterisation. Residual urine in the bladder may lead to urinary tract infection. FIG. 3 illustrates how the prior art catheter 100 then has to be moved up and down to try to alleviate pooling of residual urine. However, this moving up and down of the catheter may lead to the situation illustrated in FIG. 4, namely that urethral tissue 21 from the bladder 10 or the upper urethra 20 enters into the drainage openings and thus be subjected to chafing during the movement of the catheter up and down.

FIG. 5 illustrates an intermittent urinary catheter 1 as described herein. The urinary catheter forms a drainage conduit extending in a longitudinal direction from a proximal insertion end to a distal outlet end. The catheter is provided with a tip 2 in the proximal end. In FIG. 5, the tip is illustrated as a Nelaton tip but other tips could be applied. The tip 2 facilitates insertion into the bladder.

The urinary catheter is further provided with a connector 3 in the distal end. The connector is configured for draining urine from the drainage conduit, e.g. into an extension tube, into a collection bag, or into the lavatory.

Drainage openings 5 are positioned in a drainage portion 4. In this embodiment, the drainage openings 5 are positioned in four rows positioned in pairs with 180 degrees between the pairs. Only the two rows on one side of the intermittent urinary catheter are visible in this figure.

The catheter is for intermittent catheterisation and contains no inflatable balloons or similar means for long term fixation in the bladder.

FIGS. 6 and 7 illustrate an intermittent urinary catheter 1 as described herein positioned with the drainage portion extending into the bladder 10. In this embodiment, the tip 2 is a flex-tip. In FIG. 6, the drainage openings 5 are positioned scattered across the surface of the catheter. FIG. 6 illustrates how the plurality of drainage openings allows for inflow of urine in multiple positions. Furthermore, having this many drainage openings reduces the possibility of sucking the bladder tissue into a single drainage opening during catheterisation, as described above. FIG. 7 illustrates how the bladder 10 can be completely emptied by having this many drainage openings 5. This is because the likelihood of all of the drainage openings being blocked is very small; therefore, urine will continue to drain until the bladder 10 is completely empty. Furthermore, the drainage portion 4 is long, thus allowing for presence of drainage openings 5 at the bladder neck 11 and thereby helping to ensure emptying of the bladder 10.

Figure 8:
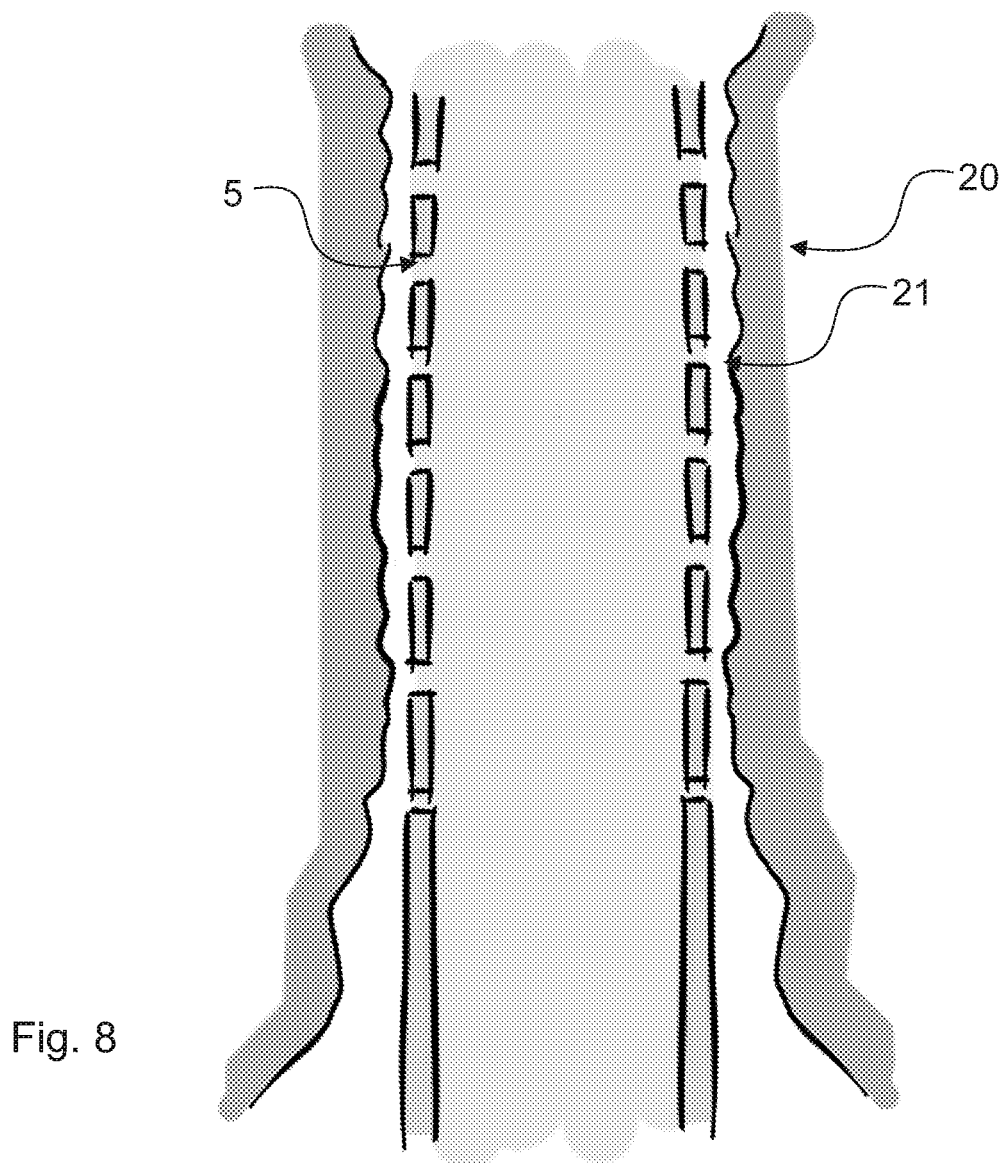

FIG. 8 illustrates a portion of an embodiment of an intermittent urinary catheter 1 as described herein positioned in the upper part of the urethra 20. The figure illustrates how the tissue 21 of the urethra will not enter in through the drainage openings 5, thereby reducing the risk of influencing the urethral tissue 20.

Figures 9A, 9B:
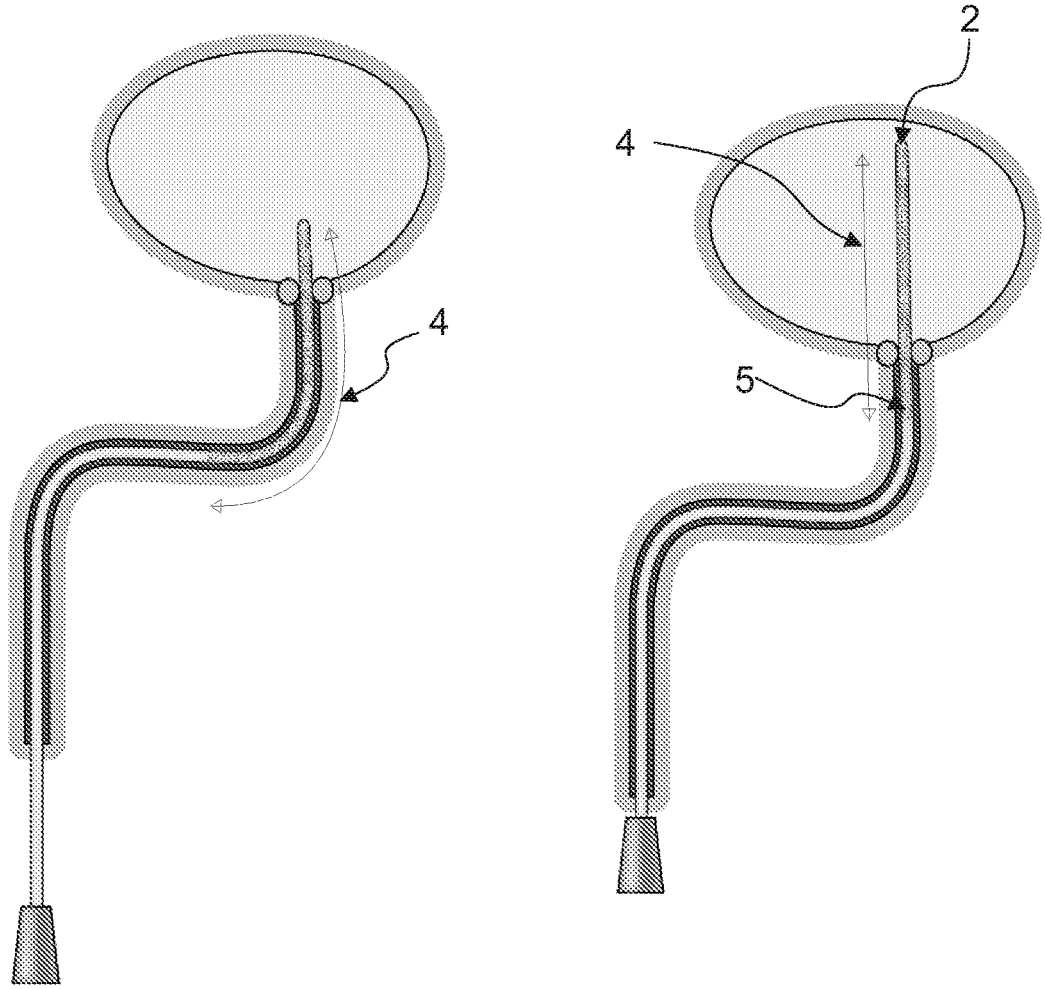

FIGS. 9A and 9B illustrate that the drainage portion 4 of a urinary catheter as described herein may be so long that even if the catheter is inserted until the tip 2 is at the top of the bladder (FIG. 9B) then the most distal of the drainage openings 5 are still positioned below the bladder neck, i.e. in the urethra.

Figure 10:
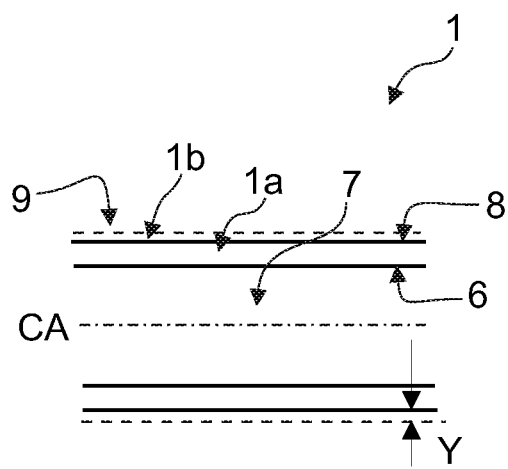
FIG. 10 illustrates an enlarged view of a cross section of a part of the catheter along the longitudinal direction indicated by the centre line CA.

FIG. 10 illustrates an enlarged view of a cross section of a part of the catheter along the longitudinal direction indicated by the centre axis CA. In this view, it is, schematically, illustrated that the catheter 1 comprises a tubular portion 1a made of a substrate material and defining an inner surface 6 towards the drainage conduit 7 and an opposite outer surface 8 facing away from the drainage conduit, the outer surface extending continuously from the proximal insertion end to the distal outlet.

That part of the outer surface which is considered for insertion into the body is covered by a layer 1b of a hydrophilic material forming a hydrophilic surface 9 of the catheter. The coating thickness Y defines a radial extent of the coating at the outer surface 8.

Figure 11:
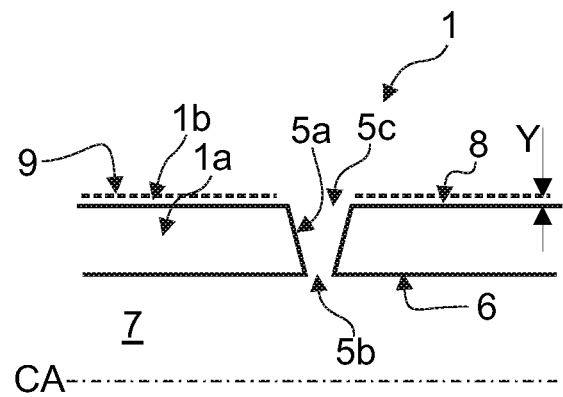
FIGS. 11-12 illustrate further enlarged views at a drainage opening 5.

FIG. 11 illustrates a further enlarged view at a drainage opening 5. Each drainage opening 5 is defined by a drainage opening wall 5a extending between an internal opening 5b in the inner surface and an external opening 5c in the outer surface. In the illustrated embodiment, the external opening 5c is larger than the internal opening such that the drainage opening wall converges from the outer surface to the inner surface.

Since the drainage openings are made by laser ablation after the hydrophilic material is deposited on the outer surface, both the hydrophilic material and the substrate material are ablated and the wall of the drainage opening is therefore not covered by the hydrophilic material.

Figure 12:
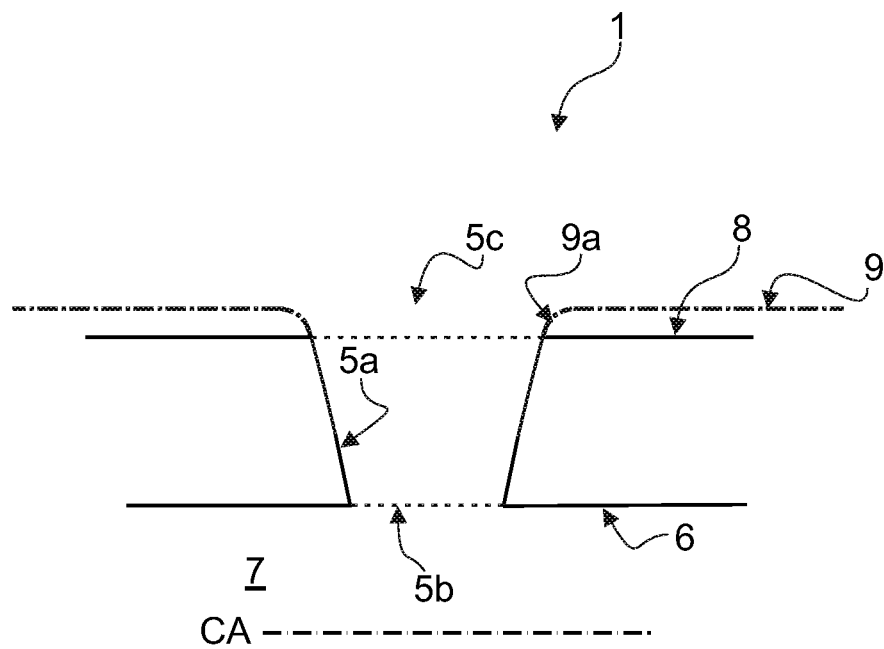

FIG. 12 illustrates a further enlarged view of FIG. 11 illustrating that the thickness of the layer 9 of hydrophilic material decreases towards each inlet opening 5c in the outer surface 8 and thereby forms a bevel 9a of the coating layer.

Figure 13:
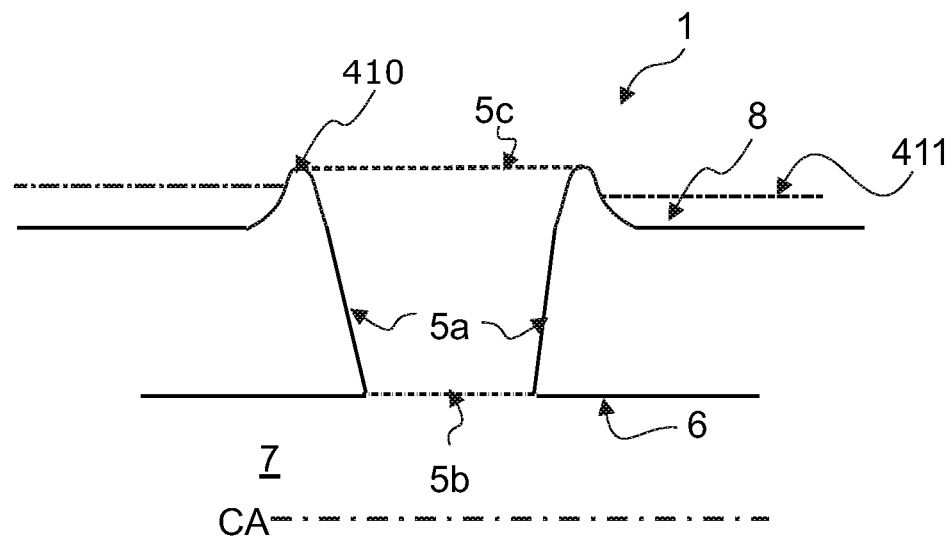
FIGS. 13-14 illustrate the projections encircling the openings in the outer surface.

FIG. 13 illustrates an embodiment of the catheter comprising projections 410 encircling the inlet openings 5c in the outer surface and extending above the hydrophilic surface 411 of the layer 9 when the hydrophilic material constituting the layer 9 is not swelled.

Figure 14:
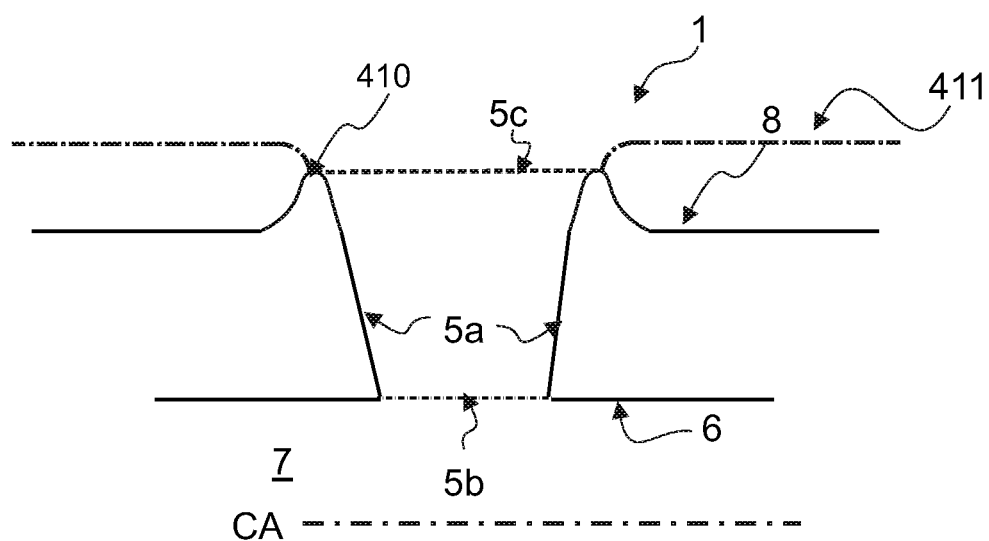

FIG. 14 illustrates the embodiment of FIG. 13 when the hydrophilic material is swelled. In this state, the hydrophilic material extends above the projections 410.

FIG. 15 illustrates the drainage part of the catheter seen from above. In this view it is shown that the drainage openings 5 are arranged in groups R1, R2, R3. The first group R1 comprises a plurality of drainage openings arranged along a first row and having an external opening 8a which is non-circular. Group R3 also has non-circular openings. The group R2 comprises a plurality of drainage openings having an external opening 8a being circular.

FIG. 16A illustrates a side view of an embodiment of an intermittent urinary catheter 1 having the drainage openings positioned in three groups, 4a, 4b and 4c. In the first group 4a, the drainage openings are positioned in a dense configuration, in the second group 4b, the drainage openings are positioned in a less dense configuration and in the third group 4c, the drainage opening are positioned even further apart.

FIG. 16B illustrates a side view an embodiment of an intermittent urinary catheter having a drainage portion 4 with drainage openings 5 positioned in three rows. Two rows are visible from in the view, but the third row is positioned on the rear side of the catheter and thus illustrated in ghost lines.

Figure 17:
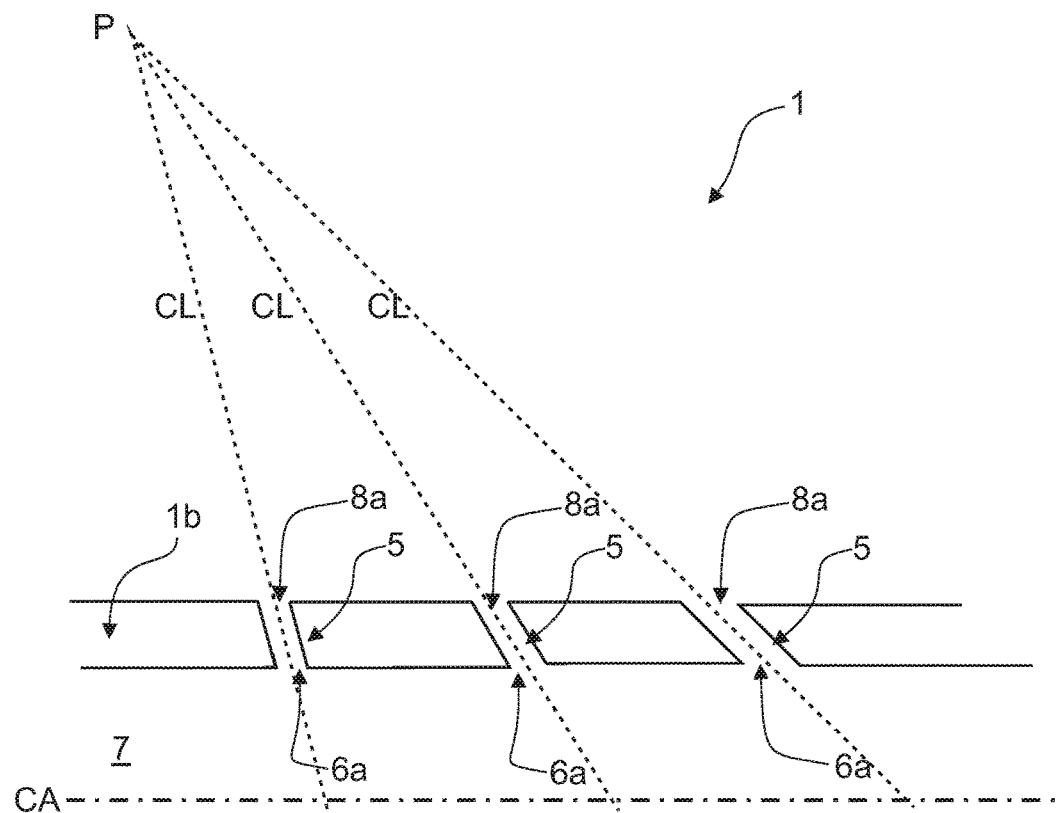
FIGS. 17 to 19 illustrate positioning of a laser emitter according to an embodiment of a method of manufacturing a catheter.

FIG. 17 illustrates an enlarged and schematic view of a cross section of a part of the catheter along the centre axis CA. In this view, it is illustrated that the catheter 1 forms a tubular wall 1b defining an inner surface 6 towards the drainage conduit 7 and an opposite outer surface 8 facing away from the drainage conduit, the outer surface extending continuously from the proximal insertion end to the distal outlet. Both the proximal insertion end and the distal outlet are outside the borders of FIG. 17.

The catheter comprises a drainage part which is considered for insertion into the body. The drainage part comprises a plurality of drainage openings 5. Each drainage opening extends along a corresponding centre line CL from an internal opening 6a into the drainage conduit 7 to an external opening 8a in the outer surface 8. The centre lines of the drainage openings intersect at an intersection point P outside the drainage conduit 7.

Figure 18:
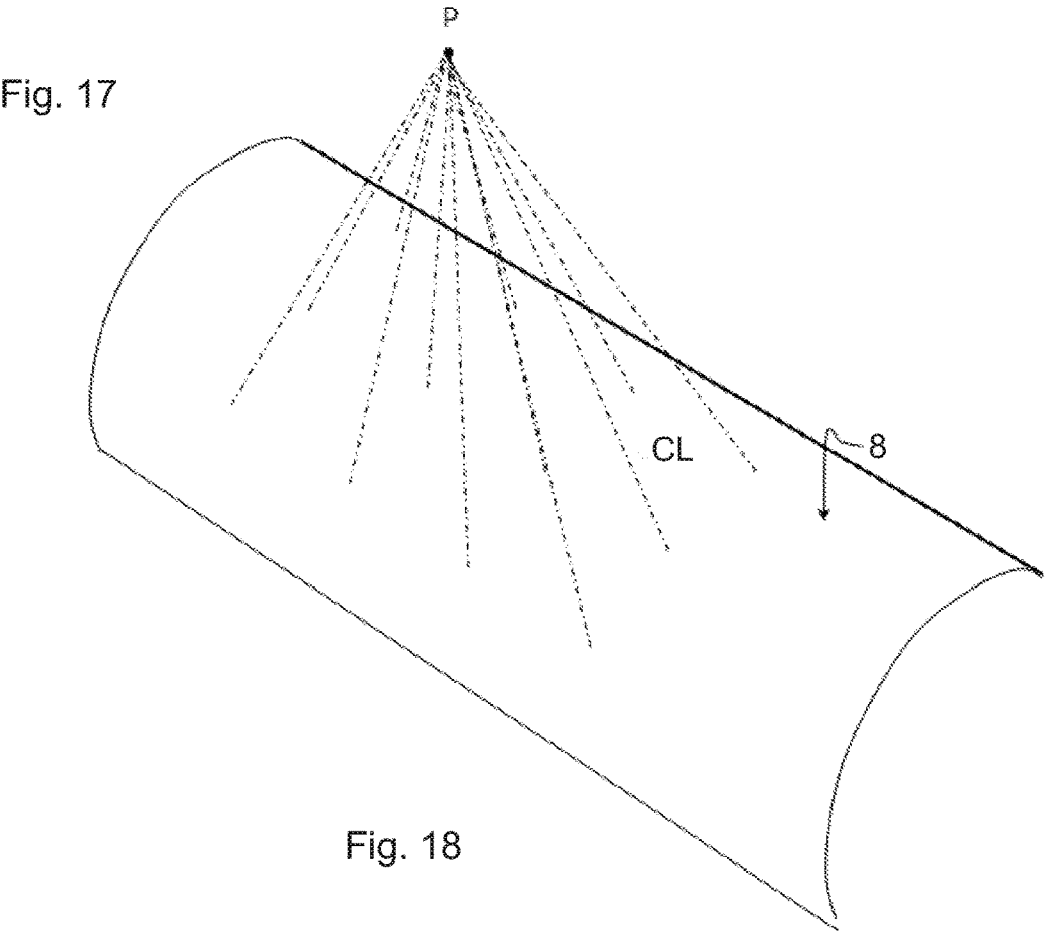

FIG. 18 illustrates a perspective view of a part of the drainage part shown in FIG. 15. In this view, it is shown that the centre lines CL of all drainage openings intersect at the intersection point P.

Figure 19:
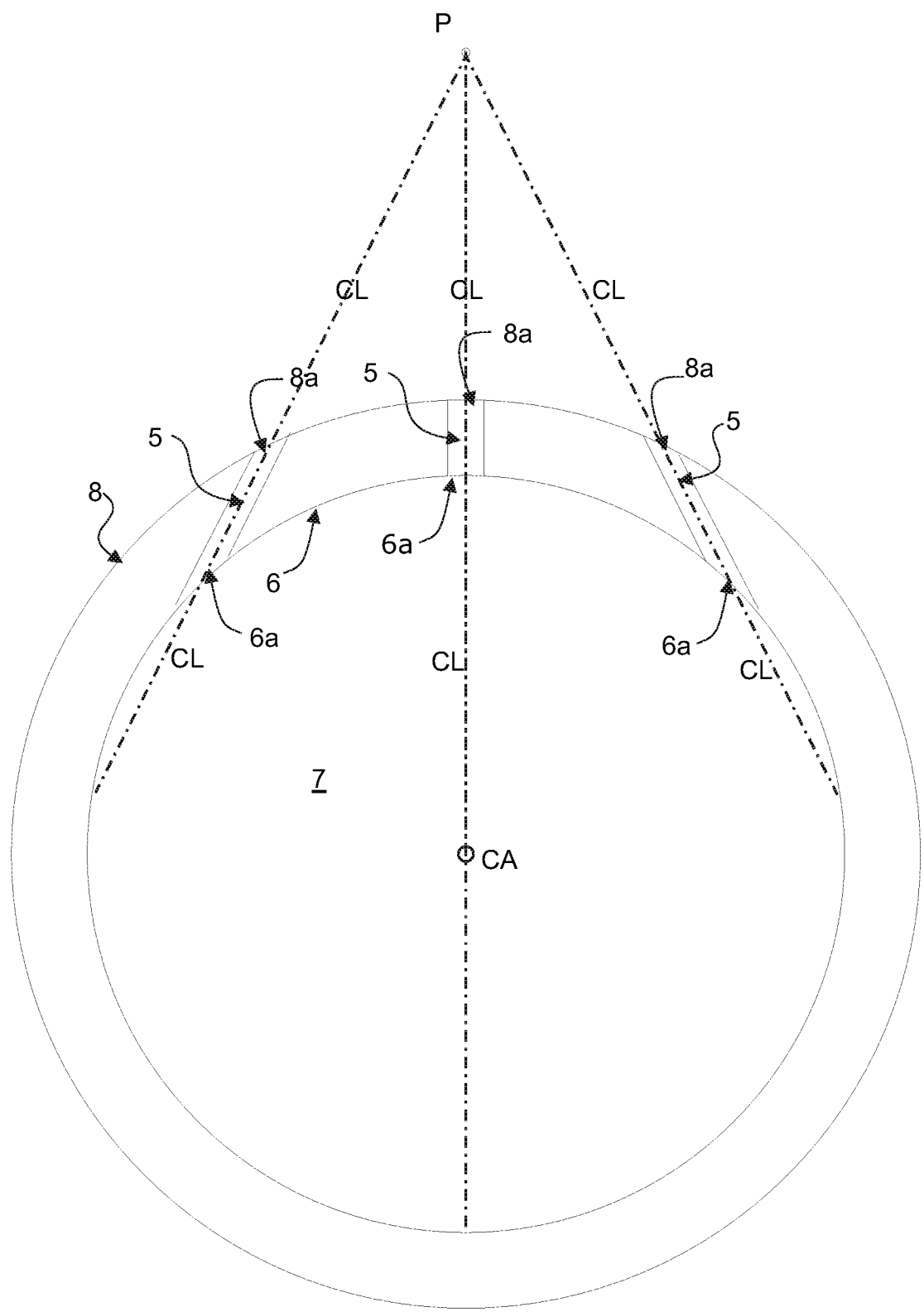

FIG. 19 illustrates a cross section transvers to the centre axis along the section AA in FIG. 15.

The drainage openings form a first, a second, and a third group R1, R2, R3 as mentioned and illustrated relative to FIG. 15. Each centre line of the first group of drainage openings intersect at least one centre line of the second group of drainage openings at the intersection point P outside the drainage conduit 7 and well above the outer surface 8.

In an alternative embodiment, a cross section of the kind shown in FIG. 19 is considered for each drainage opening in one of the groups R1, R2 or R3. In this alternative embodiment, the centre lines for one groups, i.e. the centre lines for R1, for R2 or for R3 are parallel to centre lines of the same group of drainage openings in the other cross sections while centre lines of one group of drainage openings still intersect at least one centre line of the other groups of drainage openings at the intersection point P outside the drainage conduit 7.

Figure 20:
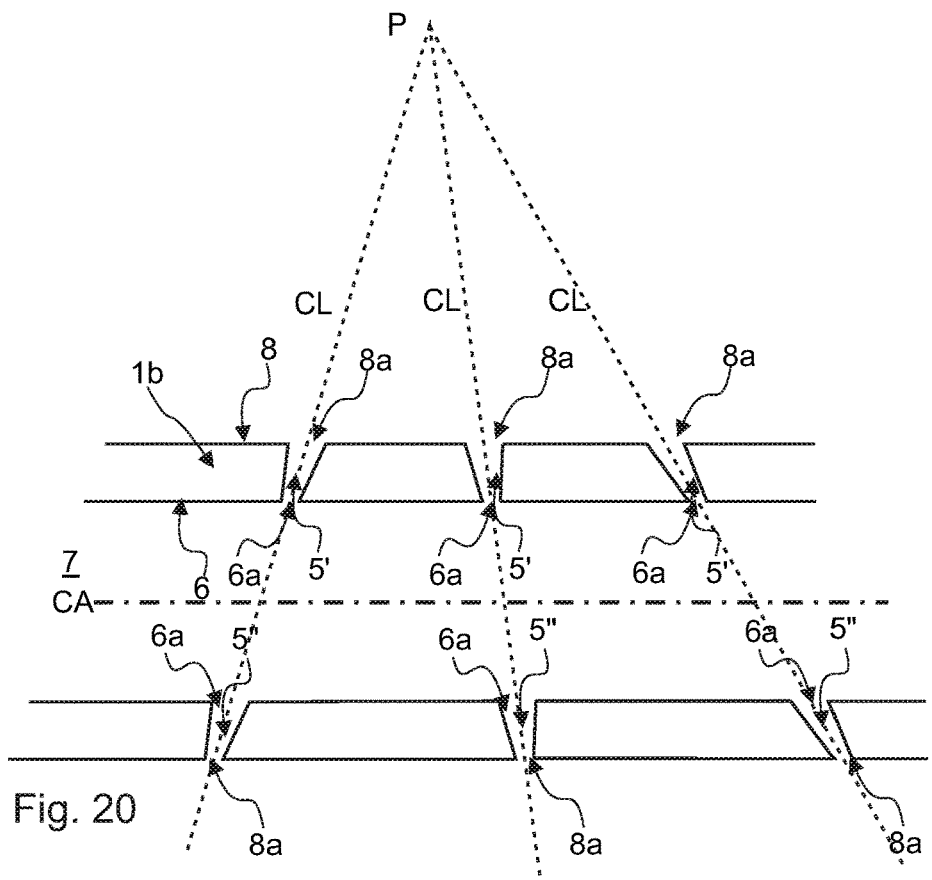
FIGS. 20 to 22 illustrate positioning of a laser emitter according to an embodiment of a method of manufacturing a catheter.

FIG. 20 illustrates an enlarged and schematic view of a cross section of a part of the catheter along the centre axis CA. In this view, it is illustrated that the catheter 1 forms a tubular wall 1b defining an inner surface 6 towards the drainage conduit 7 and an opposite outer surface 8 facing away from the drainage conduit. The outer surface extends from the proximal insertion end to the distal outlet. Both the proximal insertion end and the distal outlet are outside the borders of FIG. 20.

The catheter comprises a drainage part which is considered for insertion into the body. The drainage part comprises a plurality of drainage openings 5. Each drainage opening extends along a corresponding centre line CL from an internal opening 6a into the drainage conduit 7 to an external opening 8a in the outer surface 8.

Each drainage opening extends along a corresponding centre line from an inner surface towards the drainage conduit to an outer surface facing away from the drainage conduit, wherein the drainage openings are formed in pairs such that one pair of drainage openings comprises a first drainage opening 5' and a second drainage opening 5" both having the same centre line. Each pair of drainage openings comprises one drainage opening 5' on one side of the centre axis and another drainage opening 5" on the opposite side of the centre axis.

In the embodiment illustrated in FIG. 20, the centre lines CL of the drainage openings intersect at an intersection point P outside the drainage conduit 7.

In the embodiment illustrated in FIG. 20, the drainage openings are illustrated as converging in the upper half, meaning that the inlet opening 8a is larger than the outlet opening 6a, whereas the drainage openings in the lower half of the figure are illustrates as diverging, meaning that the outlet opening 6a is larger than the inlet opening 8a.

Figure 21:
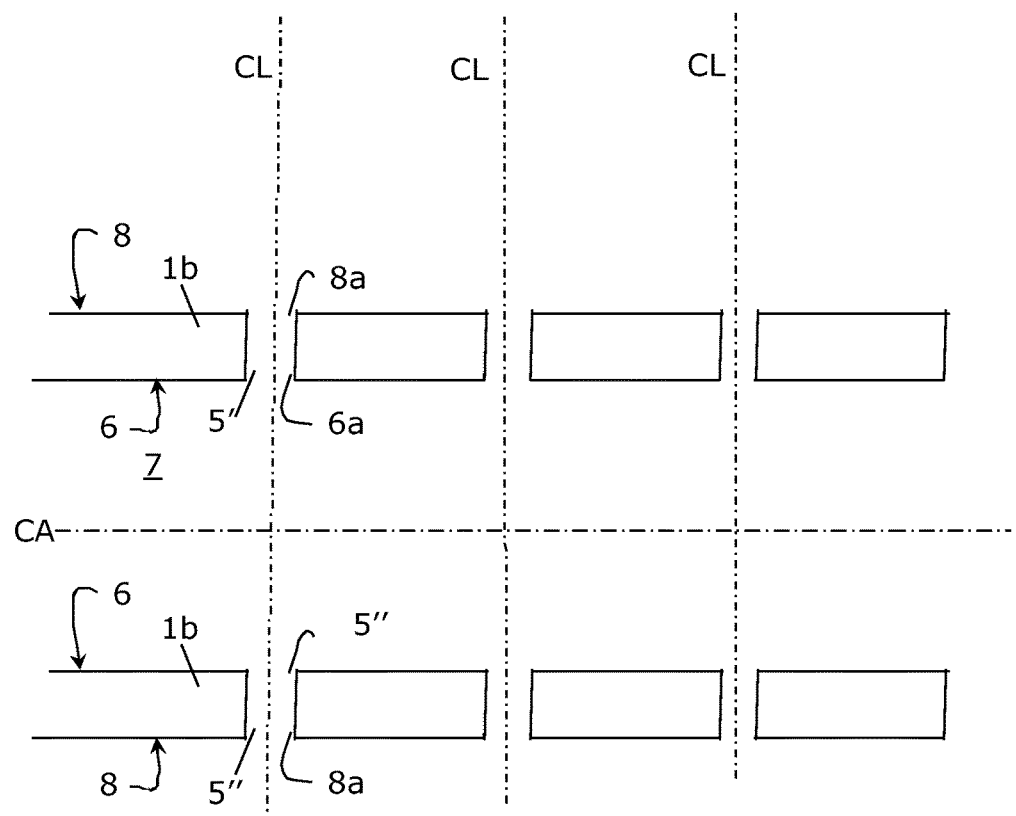

FIG. 21 illustrates an alternative embodiment in which the centre lines are parallel. In the illustrated embodiment, the drainage opening have perpendicular drainage opening walls, however, it is also contemplated that the drainage opening walls may be converging and diverging, respectively, as illustrated in FIG. 20.

Figure 22:
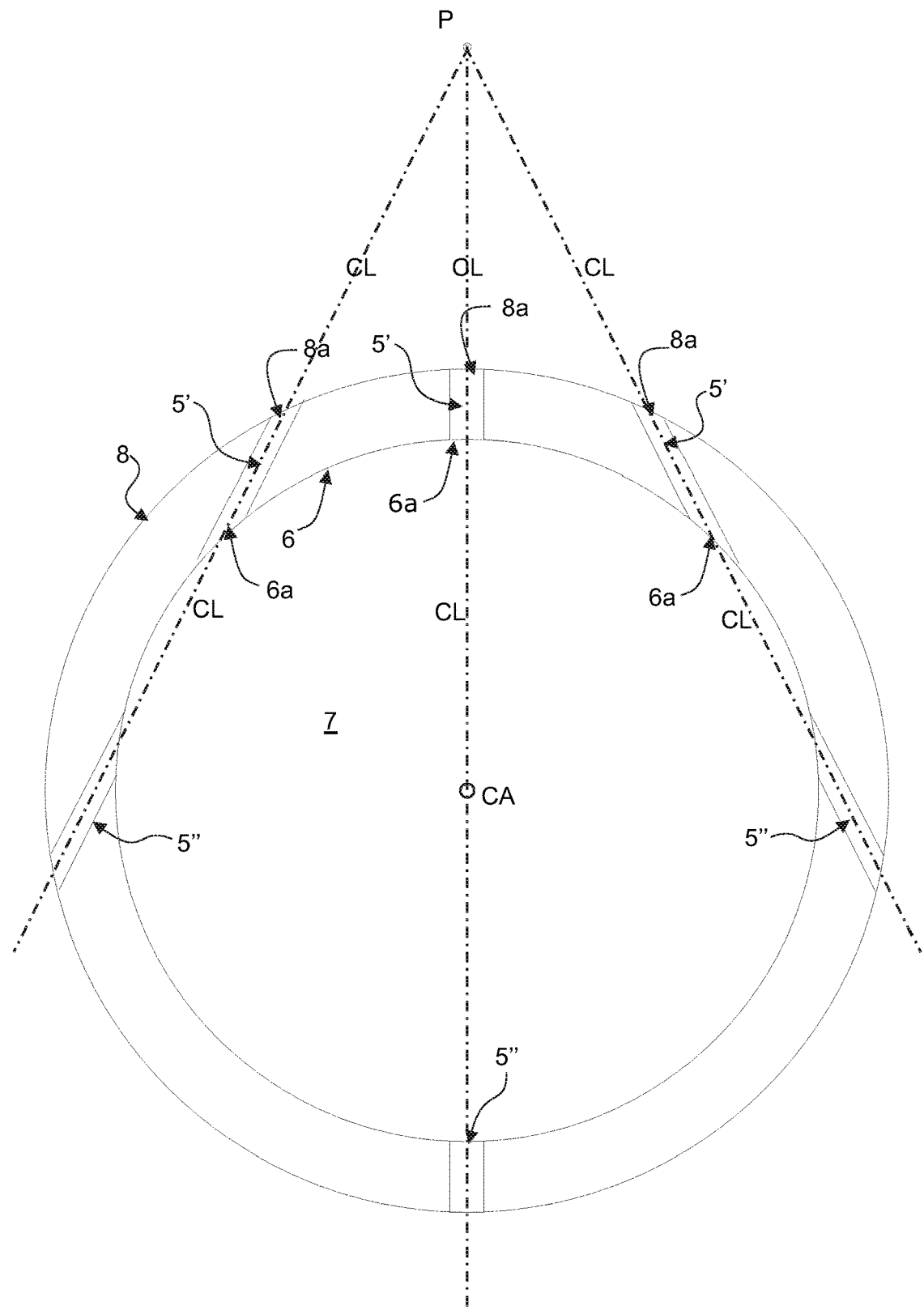

FIG. 22 illustrates a cross sectional view transversely to the centre axis along the section AA in FIG. 15. Each centre line extends through two drainage openings 5' and 5". At least the middle pair of drainage openings are on opposite sides of the centre axis CA.

The first group of drainage openings intersect at least one centre line of the second group of drainage openings at the intersection point P outside the drainage conduit 7 and well above the outer surface 8. In an alternative embodiment, the centre lines are parallel as illustrated in FIG. 21.

Figure 23:
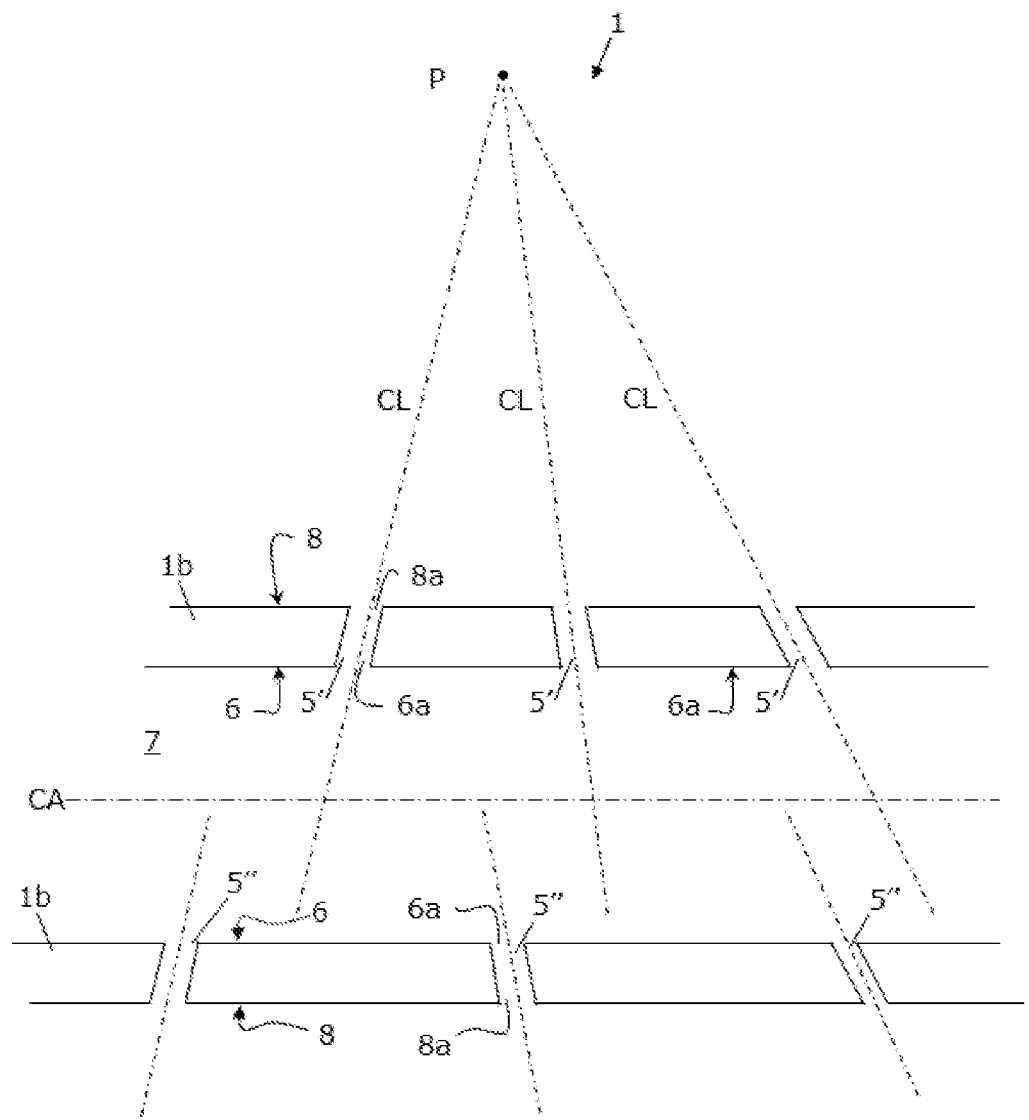
FIGS. 23 to 25 illustrate positioning of a laser emitter according to an embodiment of a method of manufacturing a catheter.

FIG. 23 illustrates an enlarged and schematic view of a cross section of a part of the catheter along the centre axis CA. In this view, it is illustrated that the catheter 1 forms a tubular wall 1b defining an inner surface 6 towards the drainage conduit 7 and an opposite outer surface 8 facing away from the drainage conduit. The outer surface extends from the proximal insertion end to the distal outlet. Both the proximal insertion end and the distal outlet are outside the borders of FIG. 23.

The catheter comprises a first drainage zone which is considered for insertion into the body. The first drainage zone comprises a plurality of drainage openings 5. Each drainage opening extends along a corresponding centre line CL from an internal opening 6a into the drainage conduit 7 to an external opening 8a in the outer surface 8.

Each drainage opening extends along a corresponding centre line from an inner surface towards the drainage conduit to an outer surface facing away from the drainage conduit, wherein the drainage openings are formed such that all drainage openings are displaced relative to each other whereby no drainage opening is located along the centre line of another drainage opening.

In the illustration of FIG. 23, the catheter comprises a first group of drainage openings 5' and a second group of drainage openings 5". The two groups are on opposite sides of the centre axis CA, but they are off-set in the direction of the centre axis CA such that no drainage openings are at the centre line of another drainage opening.

In the embodiment illustrated in FIG. 23, the centre lines of the drainage openings intersect at an intersection point P outside the drainage conduit 7.

Figure 24:
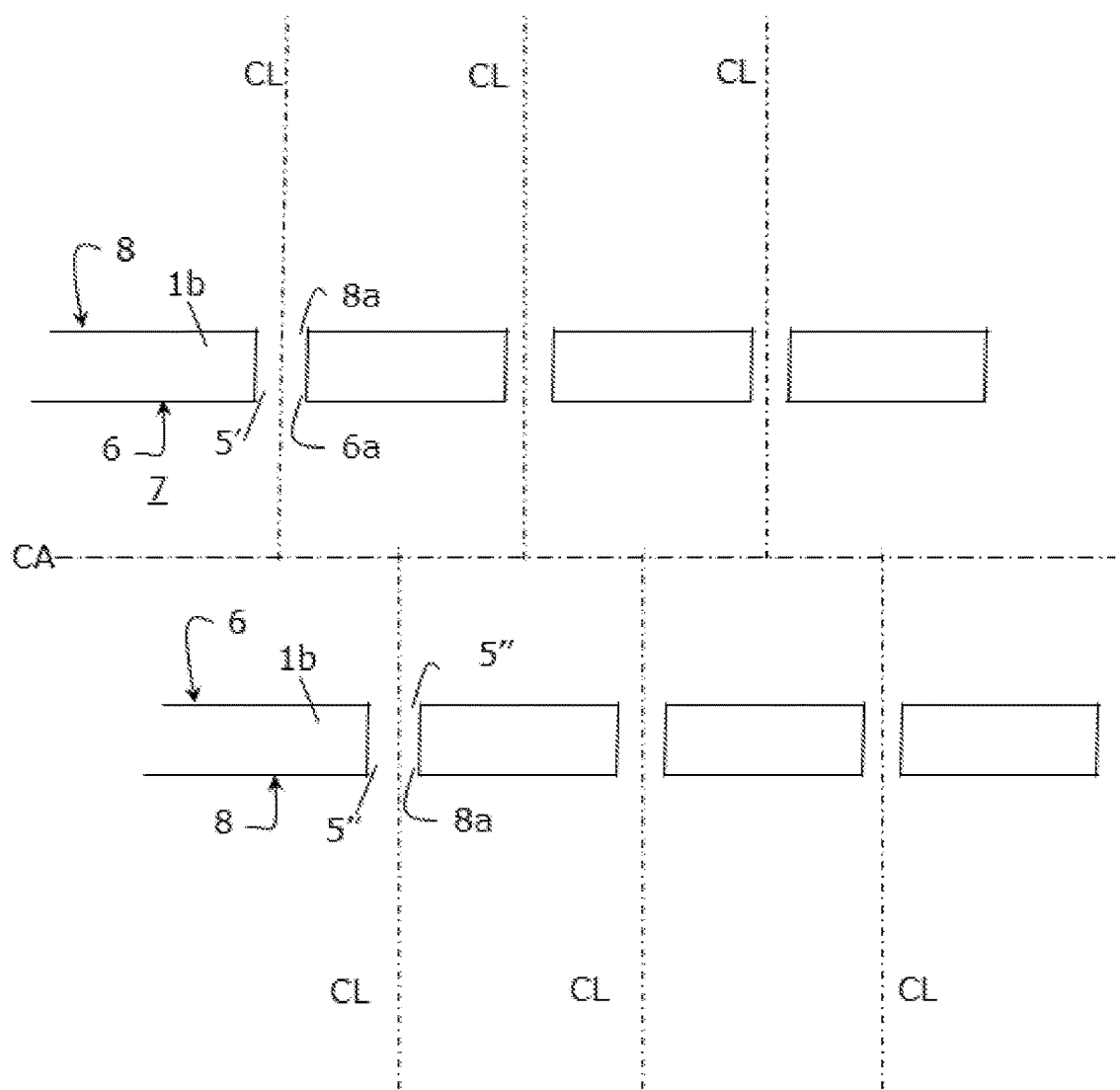

FIG. 24 illustrates an alternative embodiment in which the centre lines are parallel.

Figure 25:
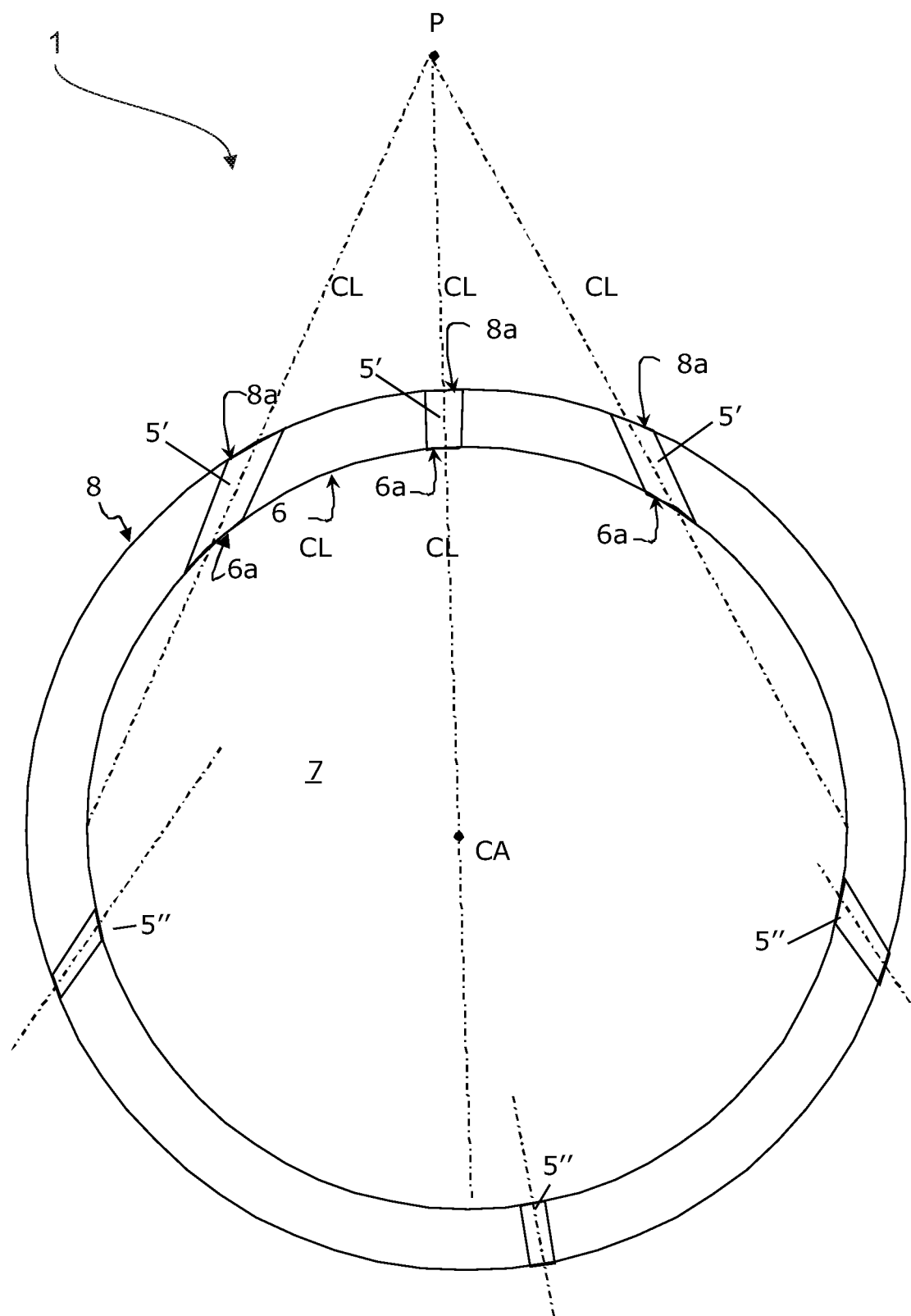

FIG. 25 illustrates a cross sectional view similar to the view in FIG. 22, however, based on a catheter portion as illustrated in FIG. 24. Each centre line extends through only one drainage opening 5' or 5" and never through two drainage openings.

The drainage openings 5' intersect at the intersection point P outside the drainage conduit 7. Common to all of the above embodiments illustrated in FIGS. 5 to 25 is that the drainage openings may effectively be made by laser ablation e.g. by a laser arranged at the point P.

FIG. 26 illustrates schematically a pressure pulse occurring in an intermittent catheter during emptying of the bladder. The figure illustrates the pressure-difference as a function of time during a series of cloggings of the drainage openings in a catheter. The pressure pulse occurs as a sudden decrease in pressure over a very short period of time—in the order of 100 milliseconds or less. It is illustrated as the peaks on the curves in the figure. As explained above, the pressure pulse occurs because the movement of the urine through the catheter is abruptly stopped due to tissue blocking the drainage openings.

FIGS. 26 to 31 illustrate results obtained by testing various catheters using the test set-up in FIG. 32-34. FIG. 26 illustrates results from testing of male catheters with a drainage height of 15-20 cm and under a level of water of 10 cm $H_2O$. Starting from the left in FIG. 26, this graph illustrates the pressure pulse obtained inside a prior art catheter of size CH16 having two regular drainage openings with a largest dimension of 5.6 mm. One of the drainage openings were closed off prior to testing. From FIG. 26, it can be seen that the pressure pulse exceeds 200 mBar. Going towards the right of the figure, the next graph illustrates the pressure pulse obtained inside a prior art catheter of size CH 12 having two drainage openings with a largest dimension of 3.9 mm. Such a catheter provides a pressure pulse of around 200 mBar. The third graph from the left illustrates the pressure pulse obtained on a prior art catheter of CH10, having drainage openings of a largest dimension of 3.4 mm. Here the pressure pulse exceeds 100 mBar. The fourth graph from the left illustrates the pressure pulse obtained on an intermittent urinary catheter as described herein and having one open drainage opening with a largest dimension of 1 mm. The graph illustrates that the pressure pulse only reaches to around 40 mBar. The graph towards the far right illustrates the pressure pulse for an intermittent urinary catheter as described herein and having one open drainage opening with a largest dimension of around 0.4 mm. Here the pressure pulse is virtually non-existent—there is almost no peak on the curve.

Figure 27:
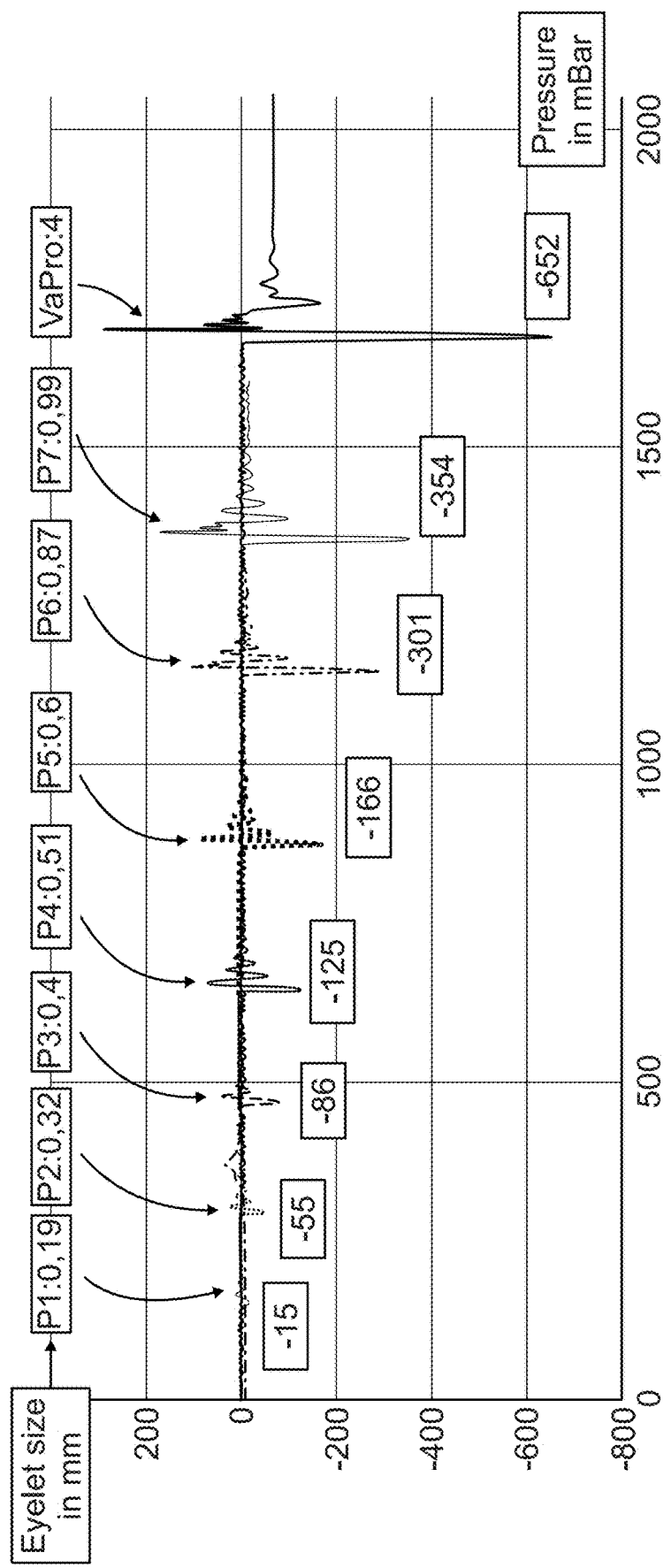

FIG. 27 illustrates results from testing of male catheters with a drainage height of 25 cm and under a level of water of 50 cm H2O. Starting from the left in FIG. 27, the graph illustrates the pressure pulses obtained in catheters with one single open drainage opening and with the single drainage opening increasing from the left in the figure towards the right. The results are also reported in Table 2 below. It can be seen that for a drainage opening of 4 mm in largest dimension, the pressure pulse (under these test-conditions) reached 652 mBar, whereas towards the left, the pressure pulse (under these test-conditions) is as low as 15 mBar when the drainage opening is 0.19 mm. Levels of less than 100 mBar is obtained with drainage openings smaller than approximately 0.4 mm, levels of less than 200 mBar is obtained with drainage openings smaller than approximately 0.6 mm and levels of less than 350 mBar is obtained with drainage openings smaller than approximately 1.00 mm.

Figure 28:
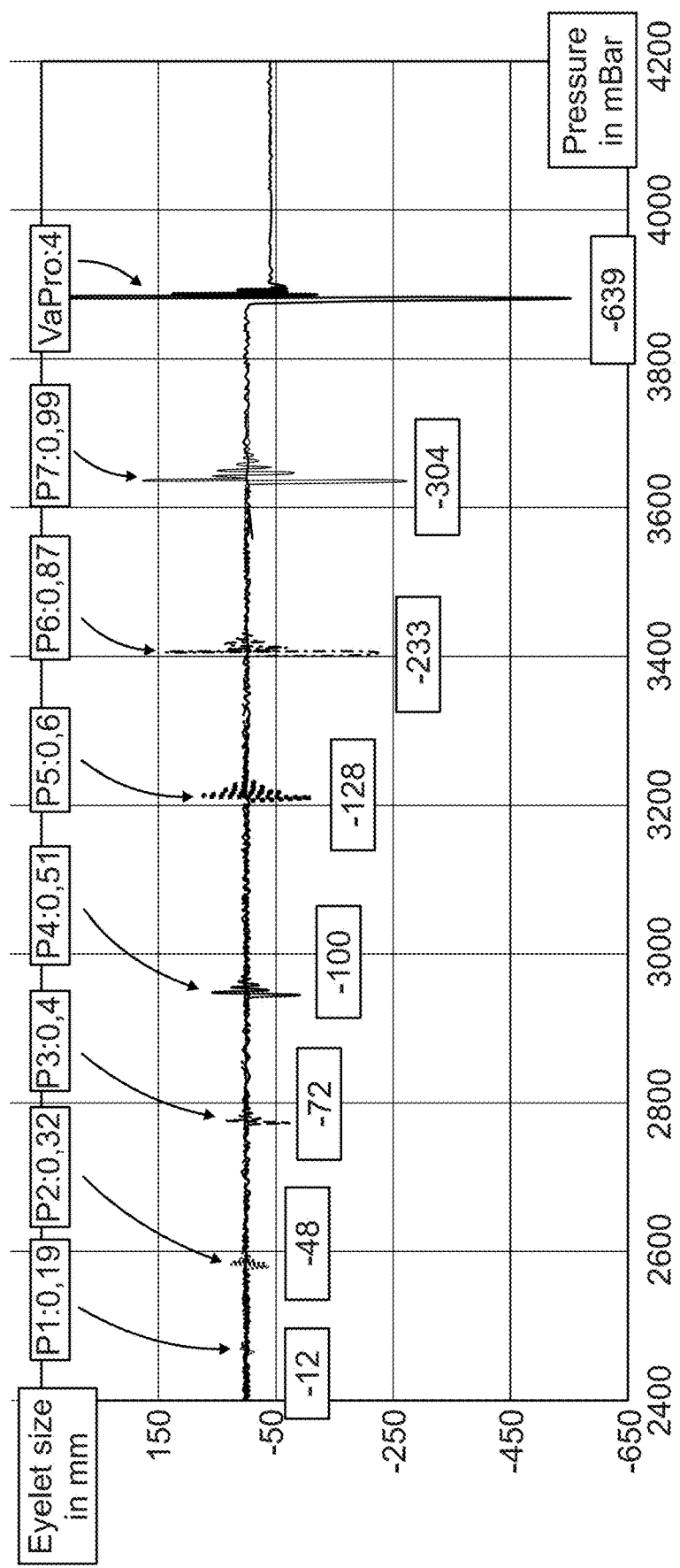

FIG. 28 illustrates results from testing of female catheters with a drainage height of 6 cm and under a level of water of 50 cm H2O. Starting from the left in FIG. 28, the graph illustrates the pressure pulses obtained in catheters with one single open drainage opening and with the single drainage opening increasing from the left in the figure towards the right. The results are also reported in Table 3 above. It can be seen that for a drainage opening of 4 mm in largest dimension, the pressure pulse (under these test-conditions) reached 639 mBar, whereas towards the left, the pressure pulse (under these test-conditions) is as low as 12 mBar when the drainage opening is 0.19 mm. Levels of less than 100 mBar is obtained with drainage openings smaller than approximately 0.5 mm, levels of less than 200 mBar is obtained with drainage openings smaller than approximately 0.7 mm and levels of less than 350 mBar is obtained with drainage openings smaller than approximately 1.00 mm.

FIGS. 29A and 29B illustrate test results for tests performed according to the test set-up in FIG. 32. FIG. 29B illustrate in larger scale a correlation between how much bladder wall or urethral tissue enters into the inner lumen through the drainage openings, the size of the drainage openings and the measured pressure pulse. From the results of the tests, it is understood that a pressure pulse below 40 mBar reduces the risk of bladder wall or urethral tissue entering into the inner lumen through the small drainage openings in the intermittent catheter and reduce the risk of influence to the tissue. In embodiments of the present disclosure, an intermittent urinary catheter is achieved wherein none or very little tissue enters into the inner lumen through the small drainage openings, when the pressure pulse is below 40 mBar. A pressure pulse below 40 mBar is obtained when the drainage opening has a largest dimension of below 0.7 mm. Thus, embodiments relate to an intermittent urinary catheter configured for providing a pressure pulse below 40 mBar. Related embodiments are an intermittent urinary catheter having drainage openings with a largest dimension below 0.7 mm.

Figure 30:
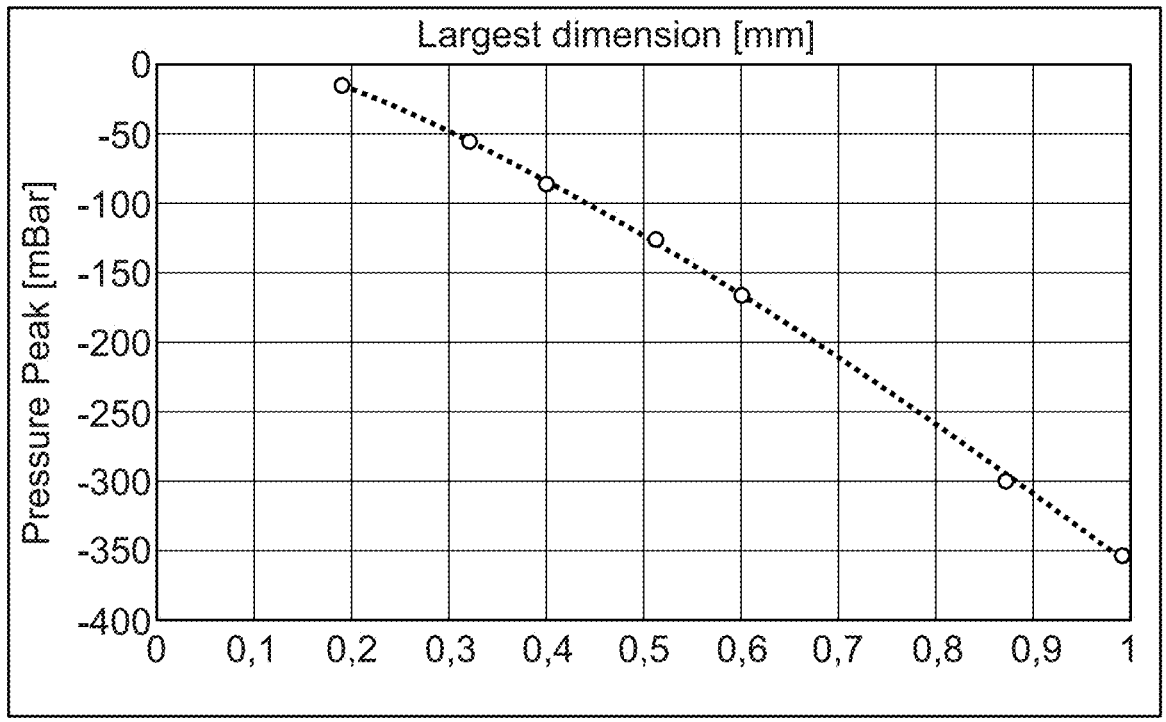
Figure 31:
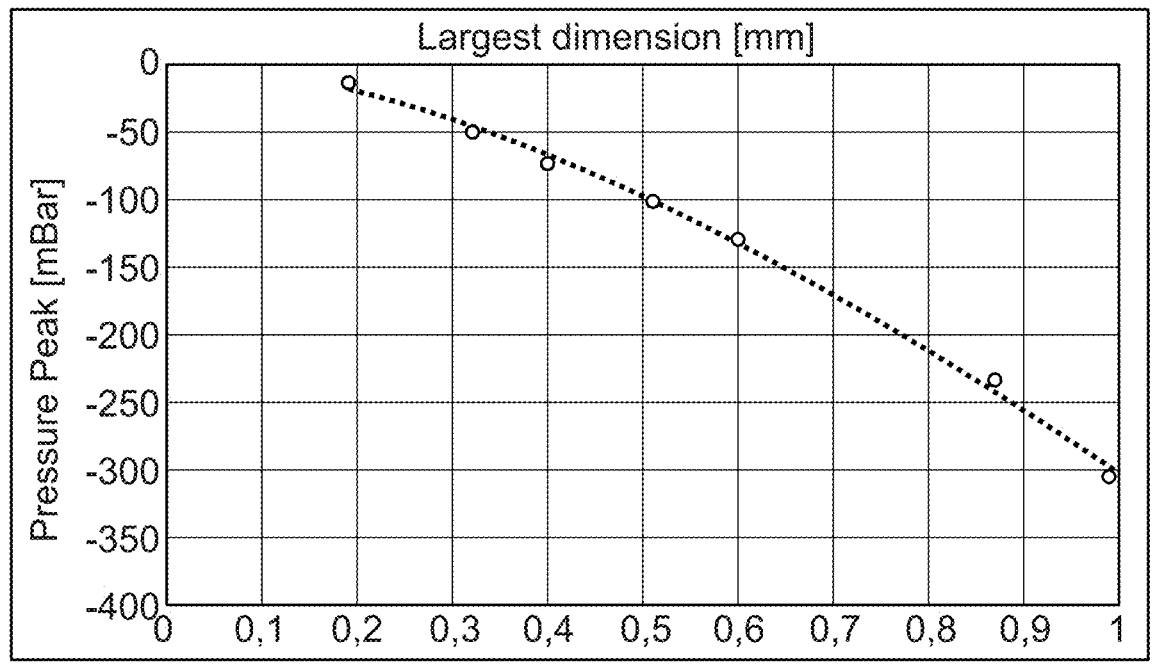

FIGS. 30 and 31 illustrate test results for tests performed according to the test set-up in FIGS. 33 and 34. The results in FIG. 30 are for testing a male catheter as illustrated in FIG. 33 and the results in FIG. 31 are results for testing a female catheter as illustrated in FIG. 34. The difference is that for the male catheter the height difference between the level of the drainage opening and the outlet of the catheter is 25 cm, wherein for the female catheter the height difference is 6 cm.

In FIGS. 30, and 31, the results of testing drainage openings with a largest dimension of 1 mm and below are shown. The curves illustrate that for a male catheter, the pressure pulse will be below 350 mBar, if drainage openings of less than 1 mm are used. For a female catheter, the pressure pulse will be below 300 mBar. If drainage openings of 0.8 mm are used, the pressure pulse for male will be around 260 mbar and for females around 210 mBar. If drainage openings of 0.4 mm are used, then the pressure pulse for male catheter will be around 90 mBar and for female around 75 mBar.

EMBODIMENTS

In the following, non-limiting and examples of embodiments of an intermittent hydrophilic urinary catheter, methods of use and methods of manufacturing such a catheter will be mentioned.

1. An intermittent hydrophilic urinary catheter defining a drainage conduit extending in a longitudinal direction from a proximal insertion end configured for insertion into a body cavity to a distal outlet end configured for draining urine from the drainage conduit, the catheter comprising a tube having a tubular wall made of a substrate material and defining an inner surface towards the drainage conduit and an opposite outer surface facing away from the drainage conduit, wherein at least an insertable part of the outer surface is covered by a layer of a hydrophilic material configured to change from a non-swelled condition to a swelled condition by contact with a swelling medium, the hydrophilic material defining a hydrophilic surface of the catheter at a coating thickness on the outer surface, and wherein the catheter comprises a plurality of drainage openings each defined by a drainage opening wall extending between an outlet opening in the inner surface and an inlet opening in the outer surface, wherein the drainage opening wall is not covered by the hydrophilic material.

2. The catheter according to embodiment 1, wherein the drainage openings are made by laser ablation of the hydrophilic material and the substrate material thereby ensuring that the drainage opening wall is not covered by the hydrophilic material.

3. The catheter according to embodiment 1 or 2, wherein the drainage opening wall has a height corresponding to the distance between the inner surface and the outer surface.

4. The catheter according to any of the preceding embodiments, wherein the outer surface extends continuously from the proximal insertion end to the distal outlet end.

5. The catheter according to any of the preceding embodiments, wherein the coating thickness decreases towards each inlet opening in the outer surface.

6. The catheter according to any of the preceding embodiments, wherein the tubular wall of the tube has a uniform wall thickness.

7. The catheter according to any of the preceding embodiments, wherein the tube has a uniform outer surface.

8. The catheter according to any of the preceding embodiments, comprising projections encircling the inlet openings in the outer surface and extending above the hydrophilic surface when the hydrophilic material is in the non-swelled condition.

9. The catheter according to embodiment 8, wherein the hydrophilic material extends above the projections when the hydrophilic material is in the swelled condition.

10. The catheter according to any of the preceding embodiments, wherein the drainage openings have a cross-sectional area of less than 0.4 mm$^2$.

11. The catheter according to any of the preceding embodiments, wherein the proximal insertion end forms a closed tip.

12. The catheter according to embodiment 11, defining a non-drainage part distally of the tip and a drainage part distally of the non-drainage part, the drainage part being provided with the plurality of drainage openings.

13. The catheter according to any of the preceding embodiments, wherein the sum of the cross-sectional area of the drainage openings is larger than the cross-sectional area of the drainage conduit.

14. A method of making a hydrophilic urinary catheter, the method comprising providing a tube made from a substrate material which defines a tubular shape with an inner surface towards a drainage conduit and an opposite outer surface facing away from the drainage conduit, coating outer surface with a hydrophilic material to define a hydrophilic surface, and providing a plurality of drainage openings from the outer surface to the inner surface by laser ablation of the hydrophilic material and the substrate material such that drainage opening walls extending between the inner surface and the outer surface are uncoated.

15. The method according to embodiment 13, wherein the tube is provided by extruding the substrate material through a die.

16. A method of reducing a local suction peak pressure in the drainage openings in the bladder as a result of blocking of the drainage openings, by using an intermittent urinary catheter as in any of embodiments 1-12.

17. An intermittent urinary catheter defining a drainage conduit extending along a centre axis from a proximal insertion end configured for insertion into a body cavity to a distal outlet end configured for draining urine from the drainage conduit, the catheter comprising a plurality of drainage openings each extending along a corresponding centre line from an internal opening into the drainage conduit to an external opening in an outer surface, wherein at least two drainage openings have centre lines intersecting at an intersection point outside the drainage conduit.

18. The catheter according to embodiment 17, where the centre lines of all drainage openings intersect at the intersection point.

19. The catheter according to embodiment 17, comprising a first group of drainage openings and a second group of drainage openings, the centre lines of the first group of drainage openings being parallel, the centre lines of the a second group openings being parallel, and each centre line of the first group of drainage openings intersect at least one centre line of the second group of drainage openings at the intersection point.

20. The catheter according to any of embodiments 17 to 19, wherein the intersecting centre lines extend at an angle of 1-4 degrees from the intersection point.

21. The catheter according to any of embodiments 17-20, wherein the intersection point is at a distance from the outer surface corresponding at least to 10 times the distance from the outer surface to the centre axis.

22. The catheter according to any of embodiments 17 to 21, wherein a first group of external openings are non circular and a second group of external openings are circular.

23. The catheter according to embodiment 22, wherein the openings of the first group of external openings extend along a straight first external line which is parallel to the centre axis.

24. The catheter according to embodiment 22 or 23, wherein the openings of the second group of external openings extend along a straight second external line which is parallel to the centre axis.

25. The catheter according to any of embodiments 17 to 24, wherein the drainage openings have a cross-sectional area of less than 0.4 mm2.

26. The catheter according to any of embodiments 17 to 25, wherein the proximal insertion end forms a closed tip.

27. The catheter according to embodiment 26, defining a non-drainage part distally of the tip and a drainage part distally of the non-drainage part, the drainage part being provided with the plurality of drainage openings.

28. The catheter according to any of embodiments 17 to 27, wherein the sum of the cross-sectional area of the drainage openings is larger than the cross-sectional area of the drainage conduit.

29. A method of making an intermittent urinary catheter, the method comprising providing a tube made from a substrate material and defining a tubular shape with an inner surface towards an internal drainage conduit and an opposite outer surface facing away from the internal drainage conduit, and providing a plurality of drainage openings extending between internal openings in the inner surface and external openings in the outer surface by laser ablation of the substrate material, wherein the laser ablation is carried out with laser light emitted from an emitter point outside the drainage conduit at an emission angle such that a first group of drainage openings is provided with a first emission angle and a second group of drainage openings is provided with a second emission angle.

30. The method according to embodiment 29, wherein the drainage openings are provided in pairs of one drainage opening from the first group of drainage openings and one drainage opening from the second group of drainage openings and where the emitter point is moved relative to the tube between each pair of drainage openings.

31. The method according to embodiment 29 or 30, wherein the distance from the emitter point to the outer surface is maintained constant when providing the drainage openings.

32. The method according to any of embodiments 29 to 31, wherein the drainage openings are provided by ablation while a pressure in the drainage conduit is changed relative to a pressure outside the drainage conduit.

33. The method according to any of embodiments 29 to 32, wherein the outer surface is coated with a hydrophilic material prior to the providing of the drainage openings.

34. A method of reducing a local suction peak pressure in the drainage openings in the bladder as a result of blocking of the drainage openings, by using an intermittent urinary catheter as in any of embodiments 17 to 28.

35. An intermittent urinary catheter defining a drainage conduit extending along a centre axis from a proximal insertion end configured for insertion into a body cavity to a distal outlet end configured for draining urine from the drainage conduit, the catheter comprising a plurality of drainage openings each extending along a corresponding centre line from an inner surface towards the drainage conduit to an outer surface facing away from the drainage conduit, wherein the drainage openings are formed in pairs such that one pair of drainage openings comprises a first drainage opening and a second drainage opening both having the same centre line.

36. The catheter according to embodiment 35, wherein the first drainage opening and the second drainage opening are on opposite sides of the centre axis.

37. The catheter according to embodiment 35 or 36, wherein each drainage opening is defined by a wall extending from an inner surface towards the drainage conduit to an outer surface facing away from the drainage conduit, wherein the wall of the first drainage opening converges in a direction from the outer surface to the inner surface and the wall of the second drainage opening diverges in the direction from the outer surface to the inner surface 38. The catheter according to any preceding embodiments 35 to 37, wherein the first drainage opening and the second drainage opening have different dimensions.

39. The catheter according to any of embodiments 35 to 38, wherein the drainage openings have a cross-sectional area of less than 0.4 mm².

40. The catheter according to any of embodiments 35 to 39, wherein the proximal insertion end forms a closed tip.

41. The catheter according to embodiment 40, defining a non-drainage part distally of the tip and a drainage part distally of the non-drainage part, the drainage part being provided with the plurality of drainage openings.

42. The catheter according to any of embodiments 35 to 41, wherein the sum of the cross-sectional area of the drainage openings is larger than the cross-sectional area of the drainage conduit.

43. A method of making an intermittent urinary catheter, the method comprising providing a tube made from a substrate material and defining a drainage conduit extending along a centre axis from a proximal insertion end configured for insertion into a body cavity to a distal outlet end configured for draining urine from the drainage conduit, and providing a plurality of drainage openings extending between internal openings in an inner surface towards the drainage conduit and external openings in an outer surface facing away from the drainage conduit, the drainage openings being made by laser ablation of the substrate material, wherein the laser ablation is carried out to form pairs of drainage openings comprising a first drainage opening and a second drainage opening provided by simultaneous ablation of the substrate material along a common centre line on opposite sides of the centre axis 44. The method according to embodiment 43, wherein the laser light emitted from an emitter point outside the drainage conduit through the internal drainage conduit.

45. The method according to embodiment 43 or 44, wherein the laser light is emitted in at least two subsequent pulses.

46. The method according to any of embodiments 43 to 45, wherein a hole size is determined for at least one of the first and second drainage opening and wherein the laser ablation is carried out in a number of shots determined by the hole size.

47. A method of reducing a local suction peak pressure in the drainage openings in the bladder as a result of blocking of the drainage openings, by using an intermittent urinary catheter as in any of embodiments 35 to 42.

The invention claimed is:

1. An intermittent urinary catheter comprising:
a tubular portion comprising a tubular wall having an inner surface and an opposite outer surface, the inner surface of the tubular wall forming a drainage conduit, the tubular portion extending in a longitudinal direction from a proximal insertion end configured for insertion into a urethra to a distal outlet end configured for draining urine from the drainage conduit;
a hydrophilic material deposited on at least an insertable part of the opposite outer surface of the tubular wall, where the hydrophilic material is configured to change from a non-swelled condition to a swelled condition by contact with a swelling medium, the hydrophilic material defining a coating thickness measured from the opposite outer surface of the tubular wall to an exposed hydrophilic surface; and
a plurality of drainage openings formed through the hydrophilic material and through the tubular wall, where formation of each of the plurality of drainage openings provides a drain opening wall extending between the inner surface and the opposite outer surface of the tubular wall with a projection encircling each of the plurality of drainage openings;
wherein the formation of each of the plurality of drainage openings removes the hydrophilic material from an entirety of each of the drain opening walls extending from the inner surface of the tubular wall to an outermost radial end of the projection encircling each of the plurality of drainage openings;
wherein the projection extends above the hydrophilic surface when the hydrophilic material is in the non-swelled condition.

2. The intermittent urinary catheter according to claim 1, wherein the hydrophilic material extends above the projection when the hydrophilic material is in the swelled condition.

3. The intermittent urinary catheter according to claim 1, wherein the coating thickness is in a range from 15-20 μm in the non-swelled condition.

4. The intermittent urinary catheter according to claim 1, wherein the coating thickness is in a range from 25-30 μm in the swelled condition.

5. The intermittent urinary catheter according to claim 1, wherein the coating thickness decreases towards each of the plurality of drainage openings.

6. The intermittent urinary catheter according to claim 1, wherein each of the plurality of drainage openings has a cross-sectional area of less than 0.4 mm².

7. The intermittent urinary catheter according to claim 1, wherein the proximal insertion end forms a closed tip.

8. The intermittent urinary catheter according to claim 7, wherein the tubular portion comprises a non-drainage portion distal of the closed tip and a drainage portion distal of the non-drainage portion, the drainage portion further comprising:
a proximal section having a first plurality of the plurality of drainage openings;
a distal section having a second plurality of the plurality of drainage openings; and
a central section located between the proximal section and the distal section and having a third plurality of the plurality of drainage openings.

9. The intermittent urinary catheter according to claim 8, wherein the drainage portion has a length of approximately 4 cm in a longitudinal direction.

10. The intermittent urinary catheter according to claim 8, wherein the drainage portion has a length of approximately 10 cm in a longitudinal direction.

11. The intermittent urinary catheter according to claim 8, wherein the drainage portion has a length of approximately 15 cm in a longitudinal direction.

12. The intermittent urinary catheter according to claim 8, wherein the drainage portion has a length of approximately 2 cm in a longitudinal direction.

13. The intermittent urinary catheter according to claim 8, wherein the first plurality of drainage openings in the proximal section is larger than the second plurality of drainage openings in the distal section.

14. The intermittent urinary catheter according to claim 8, wherein the first plurality of drainage openings in the proximal section is larger than the third plurality of the plurality of drainage openings in the central section.

15. The intermittent urinary catheter according to claim 8, wherein the first plurality of drainage openings in the proximal section is larger than the third plurality of the plurality of drainage openings in the central section, and the third plurality of the plurality of drainage openings in the central section is larger than the second plurality of drainage openings in the distal section.

16. The intermittent urinary catheter according to claim 1, wherein a sum of a cross-sectional area of the plurality of drainage openings is larger than a cross-sectional area of the drainage conduit.

17. The intermittent urinary catheter according to claim 1, wherein a number of the plurality of drainage openings is more than 20.

18. The intermittent urinary catheter according to claim 1, wherein the intermittent urinary catheter is a CH10 sized intermittent urinary catheter, and the projection encircling each of the plurality of drainage openings has a largest dimension of approximately 0.4 mm measured at an orifice of a respective one of the plurality of drainage openings, and a number of the plurality of drainage openings is larger than 32.

19. The intermittent urinary catheter according to claim 1, wherein the intermittent urinary catheter is a CH12 sized intermittent urinary catheter, and the projection encircling each of the plurality of drainage openings has a largest dimension of approximately 0.7 mm measured at an orifice of a respective one of the plurality of drainage openings, and a number of drainage openings is larger than 15.

20. The intermittent urinary catheter according to claim 1, wherein each of the plurality of drainage openings extends transversely to a longitudinal direction of the tubular portion.

21. The intermittent urinary catheter according to claim 1, wherein at least two of the plurality of drainage openings have centre lines intersecting at an intersection point outside the drainage conduit.

22. The intermittent urinary catheter according to claim 1, wherein the plurality of drainage openings are formed in pairs such that one pair of drainage openings comprises a first orifice and a second orifice, and both the first orifice and the second orifice have a same centre line.

23. The intermittent urinary catheter according to claim 22, wherein the pairs of the plurality of drainage openings are located at an oblique angle with respect to a longitudinal axis of the tubular portion.

24. The intermittent urinary catheter according to claim 1, wherein a first drain opening wall of a first of the plurality of drainage openings converges in a direction from the opposite outer surface of the tubular wall toward the drainage conduit and a second drain opening wall of the plurality of drainage openings diverges in a direction from the opposite outer surface of the tubular wall to the drainage conduit.

* * * * *